US007652164B2

(12) United States Patent
Lewis et al.

(10) Patent No.: US 7,652,164 B2
(45) Date of Patent: Jan. 26, 2010

(54) PROCESS FOR THE DIRECT SYNTHESIS OF TRIALKOXYSILANE

(75) Inventors: Kenrick M. Lewis, Flushing, NY (US); Abellard T. Mereigh, Mt. Vernon, NY (US); Chi-Lin O'Young, Poughkeepsie, NY (US); Rudolph A. Cameron, Bensalem, PA (US)

(73) Assignee: Momentive Performance Materials Inc., Albany, NY (US)

( * ) Notice: Subject to any disclaimer, the term of this patent is extended or adjusted under 35 U.S.C. 154(b) by 266 days.

(21) Appl. No.: 11/283,614

(22) Filed: Nov. 21, 2005

(65) Prior Publication Data

US 2007/0060764 A1   Mar. 15, 2007

Related U.S. Application Data

(60) Provisional application No. 60/716,728, filed on Sep. 13, 2005.

(51) Int. Cl.
 C07F 7/02   (2006.01)
 C07F 7/04   (2006.01)
(52) U.S. Cl. .................. 556/470; 556/482; 556/487
(58) Field of Classification Search .............. 556/470, 556/482, 487
 See application file for complete search history.

(56) References Cited

U.S. PATENT DOCUMENTS

| 1,800,828 | A | 4/1931 | Furness |
|---|---|---|---|
| 1,867,357 | A | 7/1932 | Furness |
| 2,525,242 | A | 10/1950 | Rowe |
| 2,666,688 | A | 1/1954 | Furness |
| RE24,324 | E | 5/1957 | Furness |
| 2,924,505 | A | 2/1960 | Page, Jr. et al. |
| 3,194,749 | A | 7/1965 | Furness |
| 3,343,406 | A | 9/1967 | Branger |
| 3,428,731 | A | 2/1969 | Furness |
| 3,641,077 | A | 2/1972 | Rochow |
| 3,775,457 | A | 11/1973 | Muraoka et al. |
| 4,328,175 | A | 5/1982 | Roeckel et al. |
| 4,454,077 | A | 6/1984 | Litz |
| 4,490,337 | A | 12/1984 | Richardson |
| 4,539,041 | A | 9/1985 | Figlarz et al. |
| 4,727,173 | A | 2/1988 | Mendicino |
| 4,761,492 | A | 8/1988 | Childress et al. |
| 4,762,939 | A | 8/1988 | Mendicino |
| 4,808,406 | A | 2/1989 | Brinkman |
| 4,999,446 | A | 3/1991 | Moody et al. |
| 5,059,343 | A | 10/1991 | Halm et al. |
| 5,084,390 | A | 1/1992 | Hallewell et al. |
| 5,149,765 | A | 9/1992 | O'Lenick, Jr. |
| 5,166,384 | A | 11/1992 | Bailey et al. |
| 5,258,053 | A | 11/1993 | Forwald et al. |
| 5,334,738 | A | 8/1994 | Pachaly et al. |
| 5,362,897 | A | 11/1994 | Harada et al. |
| 5,527,937 | A | 6/1996 | Standke et al. |
| 5,714,131 | A | 2/1998 | Margaria et al. |
| 5,728,858 | A | 3/1998 | Lewis et al. |
| 5,783,720 | A | 7/1998 | Mendicino et al. |
| 5,973,177 | A | 10/1999 | Kuivila et al. |
| 6,090,965 | A | 7/2000 | Lewis et al. |
| 6,166,237 | A | 12/2000 | Simandan et al. |
| 6,380,414 | B2 | 4/2002 | Brand |
| 6,580,000 | B1 * | 6/2003 | Anderson et al. ......... 556/470 |
| 6,680,399 | B2 * | 1/2004 | Anderson et al. ......... 556/470 |
| 6,727,375 | B2 | 4/2004 | Steding et al. |
| 2002/0136685 | A1 | 9/2002 | Huato et al. |
| 2003/0032829 | A1 | 2/2003 | Lewis et al. |
| 2003/0051580 | A1 | 3/2003 | Lewis et al. |
| 2003/0065204 | A1 | 4/2003 | Lewis et al. |
| 2004/0009117 | A1 | 1/2004 | Lewis et al. |

FOREIGN PATENT DOCUMENTS

| EP | 0494837 | 1/1992 |
|---|---|---|
| EP | 0893448 | 1/1999 |
| EP | 1245271 | 10/2002 |
| JP | 55-2641 | 1/1980 |
| JP | 55-002641 | 1/1980 |
| JP | 55-28929 | 2/1980 |
| JP | 55-028929 | 2/1980 |
| JP | 01213287 | 8/1989 |
| JP | 06-306083 | 11/1994 |
| JP | 6-306083 | 11/1994 |
| JP | 10-168084 | 6/1998 |
| JP | 10-338696 | 12/1998 |
| WO | WO 02/060623 | 8/2002 |
| WO | WO 03/091159 | 11/2003 |
| WO | WO 2004/031313 | 4/2004 |

* cited by examiner

Primary Examiner—Elvis O Price
(74) Attorney, Agent, or Firm—Dominick G. Vicari

(57) ABSTRACT

The Direct Synthesis of trialkoxysilane is carried out by conducting the Direct Synthesis reaction of silicon and alcohol, optionally in solvent, in the presence of a catalytically effective amount of Direct Synthesis catalyst and an effective catalyst-promoting amount of Direct Synthesis catalyst promoter, said promoter being an organic or inorganic compound possessing at least one phosphorus-oxygen bond.

34 Claims, No Drawings

US 7,652,164 B2

PROCESS FOR THE DIRECT SYNTHESIS OF TRIALKOXYSILANE

CROSS REFERENCE TO RELATED APPLICATION

This application claims priority to U.S. provisional application Ser. No. 60/716,728, filed Sep. 13, 2005, the entire contents of which are incorporated by reference herein.

FIELD OF THE INVENTION

This invention relates to the Direct Synthesis of trialkoxysilane by the catalyzed reaction of silicon with alcohol. In particular, the Direct Synthesis process of the present invention employs organic and inorganic phosphorus compounds such as copper phosphates, trialkyl phosphates and dialkyl phosphites to increase the reaction rate, promote selectivity to trialkoxysilane, control formation of tetraalkoxysilane and improve reaction stability in batchwise, semi-continuous and continuous operations.

BACKGROUND OF THE INVENTION

Trialkoxysilanes, especially trimethoxysilane, triethoxysilane and tri(isopropoxy)silane, are used in the production of silane coupling agents. One method of synthesis of trialkoxysilanes is directly from silicon and an alcohol in the presence of copper or a copper compound. This method is known variously in the art as the Direct Synthesis, the Direct Reaction, the Direct Process or the Rochow Reaction. For trialkoxysilanes, it is most conveniently performed in slurry reactors.

In a slurry reactor for the Direct Synthesis of trialkoxysilane, catalytically-activated silicon particles are maintained in suspension in a thermally stable, high boiling solvent and are made to react with an alcohol at an elevated temperature. The product stream exiting the reaction zone comprises a mixture of unreacted alcohol, trialkoxysilane, tetraalkoxysilane, alkyldialkoxysilane, alkyltrialkoxysilane and condensed silicates. Trialkoxysilane is usually the desired product. However, there are instances in which the tetraalkoxysilanes and alkyldialkoxysilanes are also sought and methods and processes which increase the formation of these co-products are known in the art. The trialkoxysilane product and desired co-products are typically recovered by distillation.

The rate of the Direct Synthesis of a trialkoxysilane is the temporal consumption of the raw materials (that is, alcohol or silicon), or the temporal formation of products (trialkoxysilane,optionally including by-products). Familiar units are weight percent silicon conversion per hour, or kilograms product per kilogram silicon per hour.

Selectivity is the preference for the trialkoxysilane under the reaction conditions. It is expressed herein as the gravimetric ratio trialkoxysilane/tetraalkoxysilane. Alternatively, selectivity can be expressed as mole percentage, i.e., 100 moles trialkoxysilane/molar sum of all silicon-containing products.

Stability is the maintenance of desirable rate and selectivity until all raw materials are consumed, or consumed beyond a preset criterion. The progress of the Direct Synthesis can be monitored by determining product composition and/or reaction rate as a function of time or silicon conversion. In general, the reaction profile shows an initial period (referred to as the induction period) of increasing rate and increasing trialkoxysilane concentration in the reaction mixture, after which the reaction settles into a steady state. In this state, the composition of the reaction mixture remains approximately constant. A period of declining rate and decreasing trialkoxysilane content in the product mixture follows the steady state.

It is generally accepted that the actual catalysts in the Direct Synthesis of silicon are the copper-silicon alloys or intermetallics and solid solutions formed by the diffusion of copper into silicon, or by the reaction of copper compounds with silicon. Thus, the copper-containing raw materials effective in activating silicon for the Direct Synthesis with alcohols are all catalyst precursors and will be referred to as such. A wide variety of such precursors has been disclosed in the prior art.

U.S. Pat. No. 3,641,077 discloses the slurry-phase preparation of trialkoxysilanes by directly reacting copper-silicon mass, suspended in silicone oil, with alcohol at 250-300° C. The copper-silicon mass contains about 10 weight percent copper and is prepared by heating copper and silicon above 1000° C. in a furnace in a stream of hydrogen gas.

U.S. Pat. No. 3,775,457 discloses the use of cuprous chloride and HF or HCl in the slurry-phase Direct Synthesis of silicon and alcohols. Ammonium chloride is used to restore waning reactivity.

Japanese Patent Publication 55-28929 (1980) acknowledges that activation of silicon with CuCl does not always lead to desirable rate and selectivity. The patent teaches treatment of CuCl with nitrites, naphthalenes, biphenyls and anthracenes prior to its use in the Direct Synthesis.

Japanese Patent Publication 55-2641 (1980) discloses the use of cyclic ethers such as dibenzo-18-crown-6 to improve the reaction rate and the yield of trialkoxysilane.

U.S. Pat. No. 5,362,897 discloses the use of specially prepared "wet process" CuCl, in preference to commercial "dry process" CuCl, and silicon containing 0.30-0.37 weight percent aluminum to obtain high reaction rates and silicon conversions. "Wet process" CuCl is defined (column 2, lines 51-54) as that "prepared through the steps of crystallization and separation and drying. Dry process CuCl is prepared from metallic copper and chlorine gas (column 2, lines 62-65).

U.S. Pat. No. 5,527,937 discloses a slurry-phase process for the Direct Synthesis of triethoxysilane wherein CuCl is the copper source, tri- and tetra-toluenes and/or their alkyl-substituted derivatives are the solvents and dimethylsilicone oils are employed as antifoaming agents. The method by which CuCl was prepared is not disclosed.

Japanese Patent Application 3-354055 (1991) discloses the use of copper alkoxides, with or without copper chlorides, as catalyst precursors for the Direct Synthesis of trialkoxysilanes.

Japanese Patent Application 6-306083 (1994) discloses improved selectivity and rate for the Direct Synthesis of trialkoxysilanes are realized when a an organosulfur compound such as a mercaptan, disulfide, thioheterocyclic (e.g., thiophene) or and Cu(II) thio-complex (e.g., bis(4-methylthiophenol)copper(II) is present in the reaction slurry catalyzed with a copper alkoxide. The patent discloses that appropriate quantities of these compounds can be added to the reaction when selectivity has decreased. Alternatively, the compounds can be introduced at the outset of the reaction or continuously in the alcohol feed.

Japanese Patent Application 10-168084 (1998) and Japanese Patent Application 10-338696 (1998) both disclose cupric oxide having a water content of less than 3000 parts per million and an average particle size of 0.1-50 micrometers as the catalyst precursor in a process for manufacturing trialkoxysilanes.

U.S. Pat. No. 6,727,375 and Standke et al., *Silicon for the Chemical Industry VI*, pp. 225-231 (2002), disclose processes for the production of halogen-free triethoxysilane comprising the reaction of ethanol with HF-treated silicon in MARLO-THERM® S (a synthetic heat-transfer medium) in the presence of copper (II) neononanoate at 190-250° C. in a bubble column.

U.S. Pat. No. 6,380,414 discloses the use of freshly precipitated CuO with surface areas $\geq$10 square meters per gram as a copper source to catalyze the Direct Synthesis of trialkoxysilanes. U.S. Pat. No. 6,410,771 discloses that fluorinated copper salts are also effective for the same purpose.

JP 01 213287 discloses a slurry-phase method for manufacturing trialkoxysilanes characterized by the use of "auxiliary catalysts" such as metal halides, sulfates, nitrates and/or phosphates in addition to a source of catalytic copper. These "auxiliary catalysts" are used at 0.0001-0.2 mole per mole of copper catalyst, preferably 0.001-0.03 mole per mole of copper catalyst. $NaH_2PO_4$ and $KH_2PO_4$ are the only phosphates specified in the disclosure. The use of $NaH_2PO_4$ was illustrated at 1.8 weight percent relative to CuCl.

U.S. Pat. Nos. 6,580,000 and 6,680,399 disclose the use of copper (II) organophosphate salts and tetraalkyl orthosilicates for the Direct Synthesis of triethoxysilane. Copper (II) organophosphates, for example copper (II) bis(diethyl phosphate), are soluble in ethanol as well as in tetraethyl orthosilicate and its oligomers. The disclosed processes produce reaction mixtures with selectivity less than one up to about three.

U.S. Pat. No. 4,727,173 discloses that the use of copper (II) hydroxide avoids limitations associated with cuprous chloride and provides a high selectivity to trialkoxysilanes. U.S. Pat. Nos. 6,580,000, 6,680,399 and 6,727,375 dispute the improvements claimed for copper (II) hydroxide and present comparative data showing superior performance of copper (II) organophosphates and copper (II) neononanoate in the Direct Synthesis of triethoxysilane.

U.S. Pat. No. 5,728,858 discloses that when copper (II) hydroxide is used in combination with an alkylated benzene solvent such as dodecylbenzene, the Direct Synthesis of trialkoxysilane becomes unstable after approximately 25-35 weight percent of the silicon has been reacted. When methanol is the alcohol reactant, at temperatures above about 220° C., trimethoxysilane content in the reaction product declines from approximately 90-95 weight percent to approximately 50-60 weight percent but recovers to between 80-95 weight percent after about 60 percent silicon conversion. Simultaneously with this loss of selectivity is the increased formation of methane, water and dimethyl ether. Methane and dimethyl ether formation indicate an inefficient use of the methanol reactant.

Water reacts with trialkoxysilanes and tetraalkoxysilanes to produce soluble, gelled and/or resinous organic silicates. Formation of these silicates represents inefficiency in the Direct Synthesis process. Additionally, the silicates contribute to foaming and incomplete recovery of the reaction solvent as disclosed in U.S. Pat. Nos. 5,783,720 and 6,090,965.

U.S. Pat. No. 5,728,858 discloses the reductive activation of copper (II) hydroxide/silicon slurries with hydrogen gas, carbon monoxide, monosilane or polyaromatic hydrocarbons to obtain desirably active, selective and stable Direct Synthesis of trialkoxysilanes in alkylated benzene solvents such as NALKYLENE® 550BL. Reductive activation affords a steady-state region between about 10-70 weight percent silicon conversion, increased silicon conversion and increased selectivity to trimethoxysilane.

Published U.S. patent applications 2003/0032829 and 2003/0065204 disclose that nanosized copper catalyst precursors afford superior performance in the Direct Synthesis of silanes. The nanosized copper catalyst precursors are prepared from copper (II) hydroxide and other copper sources as described in published U.S. patent applications 2003/0051580 and 2004/0009117.

There appears to be disagreement in the prior art about the effectiveness of copper (II) hydroxide as a catalyst precursor. Additionally, in spite of the improvements and advances taught in the cited prior art, there is a need for higher stability, selectivity and rate, improved raw materials efficiency and controlled by-product formation and less waste generation in the Direct Synthesis of trialkoxysilanes. In particular, there is a need for a Direct Synthesis of trimethoxysilane which produces less than 10 weight percent, and preferably less than 6 weight percent, tetramethoxysilane. There is also a need for a Direct Synthesis in which the formation of useful by-products (also termed co-products) such as $CH_3SiH(OCH_3)_2$ can be controllably increased.

Bearing in mind the problems and deficiencies of the prior art, it is an object of the invention to provide a Direct Synthesis process for producing trialkoxysilane from silicon metal and methanol and higher alcohols with reduced co-production of tetraalkoxysilane.

In is another object of the invention to provide such an improved Direct Synthesis process comprising the use of organic and inorganic phosphates, phosphonates and phosphites as additives to increase and/or maintain reaction rate at desirable values and avoid or reduce deactivation, and increase silicon conversion, while maintaining selectivity at desirably high values.

Yet another object of the invention is to utilize the aforesaid phosphorus-containing additives as nanosize materials when they are in solid form.

SUMMARY OF THE INVENTION

By way of meeting the foregoing objects as well as other objects of the invention, there is provided a process for the Direct Synthesis of trialkoxysilane which comprises conducting the Direct Synthesis reaction of silicon and alcohol, optionally in solvent, in the presence of a catalytically effective amount of Direct Synthesis catalyst and an effective catalyst-promoting amount of Direct Synthesis catalyst promoter, said promoter being an organic or inorganic compound possessing at least one phosphorus-oxygen bond.

The process of this invention results in the production of trialkoxysilane with significantly reduced levels of tetraalkoxysilane by-product while providing, inter alia, good reaction rates at desirable values, avoiding or reducing deactivation, increasing silicon conversion and maintaining selectivity at high levels, particularly in continuous and semi-continuous operations.

DETAILED DESCRIPTION OF THE INVENTION

The process whereby silicon and alcohol are converted into trialkoxysilane and co-products involves physical and chemical phenomena occurring both simultaneously and sequentially. Adequate chemical activity (reaction rate) and selectivity over a certain time period (duration of conversion) are necessary to fulfill specified economic and process engineering requirements. If activity and selectivity decline sharply after attaining desirable values and thereby limit the conversion of raw materials to trialkoxysilanes, then the process is inefficient and unstable. Stability is the maintenance of desirable rate and selectivity until all raw materials are consumed, or consumed beyond a preset criterion. Thus, a steady-state period during which rate and selectivity plateau and are relatively constant contributes to effective process control and efficient raw material utilization.

The following equations are representations of the principal chemical reactions occurring during the Direct Synthesis of trialkoxysilanes with alcohols:

$$Si + 3ROH \rightarrow HSi(OR)_3 + H_2 \tag{1}$$

$$HSi(OR)_3 + ROH \rightarrow Si(OR)_4 + H_2 \tag{2}$$

$$ROH + H_2 \rightarrow RH + H_2O \tag{3}$$

$$2ROH \rightarrow ROR + H_2O \tag{4}$$

$$RCH_2OH \rightarrow R'CH=CH_2 + H_2O \tag{5}$$

$$2Si(OR)_4 + H_2O \rightarrow (RO)_3SiOSi(OR)_3 + 2ROH \tag{6}$$

$$2HSi(OR)_3 + H_2O \rightarrow H(RO)_2SiOSi(OR)_2H + 2ROH \tag{7}$$

$$2HSi(OR)_3 + Si(OR)_4 + H_2O \rightarrow HSi(RO)_2SiOSi(OR)_2OSi(OR)_2H + 2ROH \tag{8}$$

$$RCH_2OH \rightarrow RCHO + H_2 \tag{9}$$

$$RCHO + 2RCH_2OH \rightarrow RCH(OCH_2R)_2 + H_2O \tag{10}$$

$$RR''CHOH \rightarrow RR''CO + H_2 \tag{11}$$

The desirable products of the instant Direct Synthesis are trialkoxysilanes of general formula, $HSi(OR)_3$, and alkyldialkoxysilanes of general formula, $RSiH(OR)_2$, wherein R is an alkyl group of from 1 to 6 carbon atoms. R is preferably methyl, ethyl, propyl or isopropyl. By-products of the synthesis include $Si(OR)_4$, $RSi(OR)_3$, linear, branched and cyclic silicates such as $(RO)_3SiOSi(OR)_3$, $H(RO)_2SiOSi(OR)_2H$, $HSi(RO)_2SiOSi(OR)_3$, $(RO)_3SiOSi(OR)_2R$, $(RO)_3SiOSi(RO)_2OSi(RO)_3$, $(RO)_3SiOSi(OR)HOSi(OR)_3$, $(RO)_3SiOSi(OR)ROSi(OR)_3$, $(RO)Si[OSi(OR)_3]_3$, $(RO)_3SiOSi(OR)(OSi(RO)_3)OSi(OR)_3$, $[OSi(OR)_2]_n$, wherein n is at least 4 and in which R is as previously defined, hydrogen gas, hydrocarbons such as methane and ethane, alkenes such as ethylene, ethers such as dimethyl ether and diethyl ether, aldehydes such as acetaldehyde, acetals such as 1,1-diethoxyethane and ketones such as acetone. Hydrogen gas, hydrocarbons, volatile aldehydes, ketones and the ethers are typically not condensed with the liquid products but exit the apparatus as a gaseous stream. Some of the silicates are volatilized out of the reactor and are soluble in the liquid reaction product. Others remain solubilized in the solvent or precipitate as insoluble gels. The acetals and less volatile aldehydes and ketones are condensed in the liquid reaction mixture.

The gaseous product stream contains hydrogen gas, hydrocarbons, ethers, volatile aldehydes and ketones and inerting agents such as nitrogen or argon. Analytical methods based on gas chromatography, Fourier Transform Infra-red spectroscopy (FTIR) or mass spectrometry can be used to identify and quantify these components in the gaseous effluent. Assuming that the reaction of equation [1] produces most of the hydrogen gas in the effluent, the hydrogen generated in the Direct Synthesis can be used as an approximate measure of reaction rate and silicon conversion. Hydrocarbon and ether formation depicted in equations [3-5] and aldehyde, acetal and ketone formation in equations [9-11] can be used as measures of the inefficiency of alcohol conversion. It is desirable that less than 2 weight percent of the alcohol fed to the reaction be converted to hydrocarbons, ethers, aldehydes, acetals and ketones and most desirable than none be so converted.

Gas chromatographic (GC) analysis has been found to be a reliable and accurate technique to quantify the composition of the liquid reaction product. Other methods such as nuclear magnetic resonance (NMR) and mass spectrometry (MS) can also be used. These are particularly useful for identifying and quantifying the higher molecular weight silicates contained in the reaction product and reaction solvent. Data on the composition and weight of the reaction product and the fraction of silicon in each of the components are used to calculate the silicon conversion.

Gravimetry and atomic absorption spectroscopy are suitable methods for quantifying the silicon content of the reaction solvent. Suitable analytical procedures include those given in *The Analytical Chemistry of Silicones*, Chapter 8, A. L. Smith, Ed., Wiley & Sons Inc., NY, 1991. Soluble silicates retained in the reaction solvent are a measure of the extent to which side reactions such as those in equations 6-8 have occurred. All of these reactions depend on the presence of water, which is formed, for example, by the reaction of equations 3-5 and 10. Gels and soluble silicates contained in the reaction solvent can be removed according to the methods disclosed in U.S. Pat. Nos. 5,166,384, 6,090,965 and 6,166,237, the entire contents of which are incorporated by reference herein.

Reactions can be run in a batchwise, semi-continuous or continuous mode. In batchwise operation, a single addition of silicon and copper catalyst precursor is made to the reactor at the outset and alcohol is added continuously or intermittently, until the silicon is fully reacted, or reacted to a desired degree of conversion. In continuous operation, silicon and copper catalyst are added to the reactor initially and thereafter to maintain the solids content of the slurry within desired limits. The batchwise mode is illustrated in U.S. Pat. No. 4,727,173 and the continuous mode in U.S. Pat. No. 5,084,590, the entire contents of both being incorporated by reference herein. In semi-continuous mode, additional silicon and copper catalyst precursor are introduced to the reactor during or on completion of a batchwise reaction. Thereby, multiple silicon and copper catalyst additions are made to a single charge of solvent (see Examples 6 and 7 of U.S. Pat. No. 4,727,173). Additions are typically made towards the end of the steady-state period of each charge. Alcohol flow is usually interrupted while additions are made. After a number of such additions, tetraalkoxysilane content of the crude product increases to greater than about 6 weight percent and even to as high as about 12 weight percent. Owing to the accumulation of condensed silicates in the solvent, its viscosity and foamability both increase. It is desirable that tetraalkoxysilane content remain less than about 6 weight percent through the completion of at least 3 silicon additions, and preferably through at least 6 additions. This objective can be realized with the use of the particular organic and inorganic phosphorus compounds hereinafter described.

U.S. Pat. Nos. 4,727,173 and 5,728,858 disclose processes for the Direct Synthesis of trimethoxysilane wherein product selectivity >16, rates 5-10 percent silicon conversion per hour and overall silicon conversion >85 percent are reproducibly attainable at 220-280° C. These processes employ copper hydroxide as catalyst precursor. In batchwise reactions, a steady-state region exists from about 10 weight percent silicon conversion to about 70 weight percent silicon conversion during which the content of trimethoxysilane in the reaction mixture is approximately constant and generally >85 weight percent and the selectivity >20. However, not every copper hydroxide yields this profile. Some provide poor activity or selectivity while others afford good rates and low selectivity. A commonly observed feature of the substandard copper hydroxides is high (7-30 weight percent) tetramethoxysilane formation during the initial phase (up to about 30 percent silicon conversion) of the reaction.

When the Direct Synthesis is conducted pursuant to the present invention, trialkoxysilanes comprise at least about 80 weight percent, preferably at least about 85 weight percent, of the liquid reaction products. Typical levels of the alkyl silicates, $Si(OR)_4$, are less than 7 weight percent and preferably less than about 6 weight percent. $(RO)_2SiH_2$, $RSiH(OR)_2$ and $RSi(OR)_3$ compounds are individually less than about 3 weight percent and preferably less than about 1 weight percent. Condensed silicates are maximally about 5 weight percent and preferably less than about 0.5 weight percent. In addition to the foregoing percentage ranges, selectivity to the desired trialkoxysilanes can also be expressed as the gravimetric ratio, $HSi(OR)_3/Si(OR)_4$. By the process of this invention, this ratio is at least about 16 when computed over the total course of a reaction. This overall value is also referred to herein as the product selectivity to distinguish it from the selectivity of individual samples taken during the course of a reaction. It is preferably at least about 18 and can attain values greater than 30 during the steady-state phase of the reaction.

Reaction rate is typically expressed as silicon conversion per unit time but it can also be expressed as alcohol conversion per unit time or as space time yield (product output per unit weight of raw material per unit time). It is desirable to have reaction rates which provide a good balance between product formation and heat removal (temperature control) from the reactor. Rates greater than about 4 weight percent silicon conversion per hour, preferably from about 5-20 percent silicon conversion per hour, are desired and obtainable with the process of this invention. It is also desirable that the induction time, i.e., the interval between the onset of reaction and the attainment of both steady-state rate and product composition, be brief, preferably less than about 4 hours and more preferably less than about 1 hour. During that time, the maximum amount of silicon consumed will ordinarily be about 15 weight percent and advantageously will be less than about 10 weight percent.

Reaction stability is the maintenance of desirable rate and selectivity until all of the silicon is consumed or is consumed to a predetermined criterion. Thus, the extent of silicon conversion is a quantitative measure of reaction stability. Silicon conversions greater than about 70 weight percent, advantageously greater than about 85 weight percent and better yet greater than about 90 weight percent are desirable and can be reliably achieved by the process of this invention. The present invention also includes the use of organic and inorganic phosphates to obtain $Si(OR)_4$ reaction profiles (plot of concentration of $Si(OR)_4$ in product mixture versus reaction time, alcohol fed or silicon conversion) that remain at minimal values for longer periods compared with controls.

A. Direct Synthesis Catalyst and Precursors Therefor

The copper and copper-containing compounds useful as starting materials to activate silicon for direct reactions with an alcohol are not themselves the actual catalysts for the Direct Synthesis process. When a slurry comprising copper and/or a copper-containing compound, silicon and a thermally stable reaction solvent is heated, the copper/copper-containing compound, and silicon interact to produce the actual catalyst that reacts with the alcohol. It is generally accepted that the actual catalysts are at least one copper-silicon alloys, intermetallics and/or solid solutions formed by the diffusion of copper into silicon or by the reaction of copper/copper-containing compounds with silicon. Thus, the copper-containing raw materials are copper catalyst precursors and will be so described herein.

Copper, copper (I) oxide, copper (II) oxide, copper (I) chloride, copper (II) chloride, copper (II) hydroxide, mixed hydrous oxides (for example, $3CuO.Cu(OH)_2$), basic copper carbonate ($CuCO_3.Cu(OH)_2$), copper carboxylates, copper alkoxides, copper siloxides (for example, $[CuOSiR'_3]_4$, R'=methyl, ethyl, butyl, phenyl, other linear and branched hydrocarbyl groups) and mixtures thereof are copper sources, which can be used to activate silicon for the Direct Synthesis of trialkoxysilanes. All polymorphic forms of copper (II) hydroxide, particularly the cubic and orthorhombic polymorphs, are useful catalyst precursors for carrying out the Direct Synthesis process of the instant invention.

In one embodiment, the copper (II) hydroxide has a copper content of about 54-62 weight percent and a bulk density of about 170-230 kg/m³. Also preferred are those copper hydroxides prepared by the disclosures of U.S. Pat. Nos. 1,800,828, 1,867,357, 2,525,242, 2,666,688, Re 24,324, 2,924,505, 3,194,749, 3,428,731, 4,490,337, 4,808,406; and, U.S. Patent Application 2002/0136685, the entire contents of which are incorporated by reference herein. Copper hydroxides prepared from copper sulphate, alkali metal phosphates and alkali metal hydroxides are advantageously employed herein. Phosphate promoters can be added to copper hydroxides prepared from copper chloride or with the use of ammonia to enable them to satisfy the Direct Synthesis performance criteria of this invention.

Copper catalyst precursors with particle sizes ranging from about 1 to about 10 micrometers are effective in the process of the instant invention. However, nanosized precursors can be even more effective. Nanometer sized particles have diameters in the range of from about 1 nanometer ($10^{-9}$ meter) to about 100 nanometers ($10^{-7}$ meter). These materials are also described in the prior art as nanostructured, nanocrystalline, nanosized, nanoscale, ultrafine or superfine. Their structures and high surface-to-volume ratios make them especially desirable in catalytic, electronic, magnetic and coating (pigment) applications. When compared with the conventional copper catalysts for the Direct Synthesis of trialkoxysilanes, nanometer sized particles are 10 to 100 fold smaller in diameter. Nanosized copper sources are particularly advantageous for use herein. In a first embodiment, the nanosized precursors have particle sizes of from about 0.1 to about 600 nanometers, in a second embodiment from about 0.1 to about 500 nanometers and in a third embodiment from about 0.1 to about 100 nanometers. The preparation of nanosized copper, copper (I) chloride, copper (I) oxide, copper (II) oxide and other catalyst precursors relevant to the instant invention is disclosed in U.S. published patent applications 2003/0051580 and 2004/0009117, the entire contents of which are incorporated by reference herein. Various other physical and chemical methods are known in the art for the preparation of nanosized copper and copper compounds.

Copper catalyst precursors for use in the present invention are advantageously anhydrous, but material containing adventitious water or water of hydration is also usable. If a hydrated, copper catalyst precursor is used, provision must be made in the design of the apparatus to avoid contact of the water formed during its dehydration and thermal decomposition with the trialkoxysilane reaction product. Additionally, introduction of the reactant into the reaction slurry must be delayed until the dehydration and thermal decomposition are complete. This is usually at temperatures greater than 150-180° C. at ambient pressure.

In addition to particle size and water content, various other criteria can be used to characterize the nanosized copper catalyst precursors of this invention. BET surface area of the precursors can be as low as about 0.1 m²/g. BET surface areas greater than about 10 m²/g are preferred and those greater than about 15 m²/g are particularly preferred.

Trace impurities and extraneous matter may be present in the nanosized copper catalyst precursors depending on the method and conditions of their preparation. Thus, trace amounts of aluminum, barium, calcium, chromium, iron, lead, magnesium, manganese, nickel, phosphorus, sodium, tin and zinc may be present in the commercial CuCl, $Cu(OH)_2$, $CuCO_3 \cdot Cu(OH)_2$, and $3CuO \cdot Cu(OH)_2$ and in nanosized copper and copper oxides produced by the processes of the aforesaid published patent applications on nanosized copper and copper oxides (loc. cit.), as well as by those of U.S. Pat. Nos. 4,539,041 and 5,759,230. Tolerable and limiting quantities of the pertinent metals are defined below. Polymers, surfactants and boron contamination may be present in nanoparticulate copper generated by borohydride reduction in the presence of stabilizing polymers, or in reverse micelles and microemulsions.

Zinc content of the copper catalyst precursor is desirably less than about 2500 parts per million, preferably less than about 1500 parts per million and more preferably less than about 750 parts per million. Based on the initial weight of silicon charged to the reactor, zinc content of the reaction slurry should ordinarily be less than about 100 parts per million, and preferably less than about 50 parts per million. The other trace element which can be contained in the catalyst precursor is lead (Pb). Its concentration in the slurry should ordinarily be less than about 50 parts per million.

The copper catalyst precursors used in the Direct Synthesis process of this invention will be employed at a level which is effective to catalyze the reaction. Generally, an effective amount ranges from about 0.01 to about 5 parts by weight of catalyst precursor per 100 parts by weight of the silicon metal. The smaller particle size and higher surface area of the nanosized copper catalyst precursors preferred for use in the instant invention afford higher dispersion of the actual catalytic phases on the silicon surface. Accordingly, usage of nanosized copper catalyst precursors in amounts in the lower part of the broad range is unusually effective in initiating and sustaining selective synthesis of trialkoxysilanes. Thus, from about 0.05 to about 2 parts by weight of the nanosized copper catalyst precursor per 100 parts by weight silicon is preferred and from about 0.08 to about 1 part by weight per 100 parts by weight silicon is especially preferred. Expressed in terms of parts by weight copper per 100 parts by weight silicon, an effective range is from about 0.008-4.5 parts copper, the preferred range is from about 0.03-1.8 parts copper and the more preferred range is from about 0.05-0.9 parts.

B. Direct Synthesis Catalyst Promoter

Additives which extend silicon conversion at desirable reaction rates and selectivity to the trialkoxysilane and alkyldialkoxysilane are referred to herein as "promoters". Promoters permit operation of the Direct Synthesis to produce less than about 6 weight percent tetraalkoxysilane in batchwise, semi-continuous or continuous mode. Thus, the promoters contribute to the maintenance of desirable rate and selectivity and improve reaction stability but are not themselves catalysts for of the Direct Synthesis process.

Organic and inorganic phosphorus compounds containing phosphorus-oxygen (P—O) bonds are effective promoters for the Direct Synthesis of this invention. These compounds include phosphate salts, phosphate esters, polyphosphates, metaphosphates, pyrophosphates, phosphonates and phosphites. Definitions of these classes and the nomenclature of phosphorus compounds are set forth in D. E. C. Corbridge, Studies in Inorganic Chemistry 10: Phosphorus (4$^{th}$ edition), Elsevier, Amsterdam, 1990, chapters 3 and 4. Phosphates, phosphites, and phosphonates are the preferred classes of promoters for the practice of this invention.

Compounds containing discrete $PO_4^{3-}$ ions are orthophosphates. Pyrophosphates (diphosphates) contain the $P_2O_7^{2-}$ anion. $P_3O_{10}^{5-}$ occurs in triphosphates (also called tripolyphosphates) and $P_{n+1}O_{3n+4}^{(n+3)-}$ in polyphosphates ($n \geq 4$). The metaphosphates contain the cyclic units, $P_xO_{3x}^{x-}$ in which x is greater than or equal to 3. Typical of these metaphosphate anions are $P_3O_9^{3-}$, $P_6O_{18}^{6-}$ and $P_8O_{24}^{8-}$. In one embodiment, copper orthophosphates, copper pyrophosphate and copper metaphosphate are used as the promoters of this invention.

Inorganic phosphates are effective promoters of reaction stability in the Direct Synthesis of trialkoxysilanes. Copper orthophosphates, copper metaphosphates, copper pyrophosphate and copper polyphosphates are highly effective. Examples of useful copper phosphates include those set forth in Table 1, infra. The selected copper phosphate promoter(s) can be added to the reactor individually or in combination with the copper catalyst precursors. The promoters can also be generated in situ in the Direct Synthesis reactor from the reaction of a copper catalyst precursor and an alkali metal phosphate.

The solid phosphate promoters can be anhydrous or hydrated and are advantageously anhydrous. Particle sizes can range from between about 10 micrometers to about 0.1 nanometer. In one embodiment, the particle size of the promoter is less than about 5 micrometers and in another embodiment is from about 1 and about 600 nanometers. Particle sizes in this latter embodiment may be regarded as nanosized. A representative synthesis of nanosized copper phosphates is described in Bulletin of Materials Science, Vol. 22, pp. 335-339 (1999), the entire contents of which are incorporated by reference herein.

TABLE 1

COPPER PHOSPHATE PROMOTERS

| COMMON NAME | FORMULA | (Cu/P) RATIO | OTHER NAME(S) |
|---|---|---|---|
| Copper orthophosphate | $Cu_3(PO_4)_2$ | (3/2) = 1.5 | |
| Basic copper phosphate | $Cu_3(PO_4)_2 \cdot Cu(OH)_2$ | (4/2) = 2.0 | Libethenite |
| Basic copper phosphate | $Cu_3(PO_4)_2 \cdot 2Cu(OH)_2$ | (5/2) = 2.5 | Pseudomalachite, Reichenbachite, Ludjibaite |
| Basic copper phosphate | $Cu_3(PO_4)_2 \cdot 3Cu(OH)_2$ | (6/2) = 3.0 | Cornetite |
| Copper pyrophosphate | $Cu_2P_2O_7$ | (2/2) = 1.0 | |
| Copper polyphosphate | $Cu_5(P_3O_{10})_2$ | (5/6) = 0.83 | |
| | $CuMPO_4$ (M = $NH_4$, H, alkali metals) | (1/1) = 1.0 | |
| Copper metaphosphate | $Cu_3(P_3O_9)_2$ | (3/6) = 0.5 | |

Phosphate esters are pentavalent organic phosphorus compounds of general formulae, $(RO)_n(OH)_{3-n}PO$, in which R is $C_1$-$C_{20}$ alkyl, aryl, cycloaliphatic, or alkaryl and n is an integer from 0 to 3 inclusive. The triesters, $(RO)_3PO$, are highly effective promoters. Examples include $(CH_3O)_3PO$, $(C_4H_9O)_3PO$, $(C_8H_{17}O)_3PO$, $(CH_3O)(C_8H_{17}O)_2PO$, $(C_2H_5O)(C_4H_9O)_2PO$, $(CH_3C_6H_4O)_3PO$, $(C_6H_5O)_3PO$ and $(C_6H_5CH_2O)_3PO$. $(CH_3O)_3PO$, $(n-C_4H_9O)_3PO$ and $(C_8H_{17}O)_3PO$ are especially advantageous for use herein. In the formulae above, R can also contain functional groups which will not significantly interfere with the conduct of the desired trialkoxysilane Direct Synthesis. Thus, R can contain oxyalkylene groups and ether (—C—O—C—) linkages. Suitable examples are $(CH_3OCH_2CH_2O)_3PO$ and $(C_4H_9OCH_2CH_2O)_3PO$ and $[CH_3O(CH_2CH_2O)_a(CH_2CHOCH_3)_bO]_3PO$ wherein a=0-30 inclusive and b=0-30 inclusive.

The phosphorylated oxyalkylene group can be part of a copolymer composition such as any of those disclosed in U.S. Pat. No. 5,149,765 and sold by SILTECH Corp. under the trade name SILPHOS®. Suitable examples can be represented by the general formulae $MD_xD^*_yM$ and $M^*D_uD^*_vM^*$ in which $M=(CH_3)_3SiO_{1/2}$, $D=(CH_3)_2SiO_{2/2}$, $D^*=CH_3SiZO_{2/2}$ and $M^*=Z(CH_3)_2SiO_{1/2}$ in which Z is a phosphorlyated oxyalkylene group, u, x and y are individually greater than zero and v is greater than or equal to zero. Examples include $MD_{44}D^*_4M$ in which Z is $—(CH_2)_3(C_2H_4O)_{11.5}CH_2OP(OH)_2O$ and $M^*D_6D^*_3M^*$ in which Z is $—(CH_2)_3(C_2H_4O)_{8.5}CH_2OP(OH)_2O$.

Silicate-phosphate copolymers of the type $(ROSi)_w(R'OP=O)_z$ in which R and R' are individually C1 to C20 alkyl, aryl, cycloaliphatic, or alkaryl groups and w and z are positive numbers are also effective phosphate promoters of the instant invention. Suitable examples are $(CH_3OSi)_w(CH_3OP=O)_z$ and $(C_2H_5OSi)_w(C_2H_5OP=O)_z$ in which w and z are each broadly 0.5-25 and w is preferably 5-20 and z is preferably 1-5.

Compounds of general formula, $(RO)_3Si(CH_2)_q(R'O)_2P=O$, bearing alkoxysilane and alkylphosphate moieties are also effective promoters. R and R' have the same meaning as defined for the silicate-phosphate copolymers. The integer, q, has values from 1 to 8 and is preferably 1 to 4 inclusive. $(C_2H_5O)_3Si(CH_2)_3(C_2H_5O)_2P=O$ and $(CH_3O)_3SiCH_2(CH_3O)_2P=O$ are typical examples of these promoters.

Organophosphates derived from glycerol, mannitol, inositol, galactitol, sorbitol and other polyhydric alcohols and sugars are also promoters within the scope of the present invention. Suitable examples include glyceryl phosphates such as $HOCH_2—CHOH—CH_2OP(O)(OH)_2$ and $(HO)_2P(O)OCH_2—CHOH—CH_2OP(O)(OH)_2$ and phytic acid, the hexaphosphoric acid ester of myo-inositol.

Organophosphites are also useful as promoters in the Direct Synthesis process of this invention. They are tervalent compounds of general formulae, $(RO)_nP(OH)_{3-n}$, in which R is C1 to C20 aliphatic, cycloalpihatic, aryl, alkaryl or oxyalkylene group. $(C_2H_5O)_3P$, $(C_8H_{17}O)(C_4H_9O)_2P$ and $(C_{12}H_{25}O)_3P$ are suitable examples of triorganophosphites. Diorganophosphites, $(RO)_2POH$, exist primarily as the tautomeric phosphonate, $(RO)_2HPO$. Examples effective in the practice of this invention are $(CH_3O)_2HPO$, $(C_2H_5O)_2HPO$, $(C_4H_9O)_2HPO$, $(C_8H_{17}O)_2HPO$, $(C_6H_5O)_2HPO$ and $(C_6H_5CH_2O)_2HPO$.

Esters of diphosphates of general formula, $(RO)_mP_2O_3(OH)_{4-m}$, in which $m\geq 2$ are also effective promoters. R has the same meaning as hereinabove defined. Methyl, ethyl, butyl and octyl are preferred.

Liquid and solid phosphate promoters can be added to the reactor at the outset of the reaction, or intermittently or continuously during the process. The promoter can be introduced separately or admixed with the alcohol stream, the solvent, or silicon and copper sources, depending on considerations such as physical form, boiling point, cost, handling convenience, safety, and the like. Mixtures of promoters can be employed to effectively promote reaction stability. For example, in the Direct Synthesis of trimethoxysilane, copper phosphate can be added (alone or combined with the copper catalyst precursor) along with trimethyl phosphate (injected separately or contained in the solvent or in the methanol feed). The use of both promoters has been found to decrease $Si(OR)_4$ formation to less than about 4 weight percent of the reaction mixture and afford $HSi(OR)_3$ greater than 90 weight percent.

The promoters used in the Direct Process of this invention will advantageously be present in an amount effective to maintain $Si(OR)_4$ formation below about 6 weight percent as well as $HSi(OR)_3$ formation greater than about 85 weight percent and extend silicon conversion beyond about 88 weight percent at desirable reaction rates. Generally, the optimum amount of promoter for a given process is determined by factors such as the specific trialkoxysilane being synthesized, physical form of the phosphate promoter, the particle size of the promoter (if solid), the boiling point and surface activity of the organic phosphorus compound (if liquid) and the ease of formation of an organophosphate, organophosphonate or organophosphite from an inorganic phosphate and an alcohol under the reaction conditions. For the Direct Synthesis of trimethoxysilane, effective usage of solid inorganic phosphates such as the copper phosphates is typically from about 3-30 weight percent, and advantageously from about 4-10 weight percent, based on the weight of copper catalyst precursor charged to the Direct Synthesis. Usage based on the weight of silicon charged to the reactor can range from about 200-3000 parts per million and advantageously ranges from about 200-1500 parts per million. With liquid organophosphates such as trimethyl phosphate, the effective ranges are generally from about 100-1500 parts per million and advantageously from about 100-800 parts per million on the same basis.

C. Silicon Metal Reactant for the Direct Synthesis

The silicon metal reactant used in the process of this invention can be any commercially available grade of silicon in particulate form. It may be produced by any of the methods in current practice such as casting, water granulation, atomization and acid leaching. These methods are more fully described in *Silicon for the Chemical Industry*, (H. Oye, et al, Editors), vol. I (pp 39-52), vol. II (pp 55-80), vol. III (pp 33-56, 87-94), Tapir Publishers, Norwegian Institute of Technology, in U.S. Pat. Nos. 5,258,053, 5,015,751, 5,094,832, 5,128,116, 4,539,194, 3,809,548 and 4,539,194, and German Patent Nos. 3,403,091 and 3,343,406. Special types of chemical grade silicon containing controlled concentrations of alloying elements are also suitable provided that copper is not one of the alloying elements and that the alloying elements are not deleterious to the rate, selectivity and stability of the trialkoxysilane Direct Synthesis process. Special silicon of this type is described in U.S. Pat. Nos. 5,059,343, 5,714,131, 5,334,738 and 5,973,177, and European Patent Applications 0494837 and 0893448. A typical composition of commercial silicon metal useful in this invention, expressed in percent by weight, is Si~98.5%, Fe<1%, Al~0.05 to 0.7%, Ca~0.001 to 0.1%; Pb<0.001%, Water<0.1%. Generally, smaller particle sizes are preferred for ease of dispersion in the slurry, faster reaction and minimization of erosion in the reactor. Preferably, there are no particles larger than about 500 micrometers so that reactor erosion is minimized. Sieving of ground silicon to regulate particle size is optional. A particle size distribution wherein at least about 90 weight percent is between about 1-300 micrometers is preferred. Especially preferred is a distribution in which at least about 90 weight percent of the silicon particles is between about 20-200 micrometers.

D. Alcohol Reactant for the Direct Synthesis

Alcohol reactants which are useful in the process of this invention are those of the formula ROH wherein R is an alkyl group containing from 1 to 6 carbon atoms, inclusive. Preferably R is an alkyl group containing from 1 to 3 carbon atoms inclusive. The more preferred alcohols are methanol and ethanol. While it is customary to use a single alcohol in the Direct Synthesis process, mixtures of two or more alcohols can also be used to prepare trialkoxysilanes with different alkoxy groups, or to facilitate the reaction of a less reactive alcohol. For example, up to about 5 weight percent methanol may be added to ethanol to improve the rate and stability of the Direct Synthesis of triethoxysilane. Alternatively, the reaction can be initiated with one alcohol and continued with another, or with a mixture. Thus, copper-activated silicon prepared with nanosized copper catalyst precursors according to the instant invention can be reacted initially with methanol and later with ethanol. It is preferable that the alcohol be anhydrous. However, some water content, e.g., of up to about 0.1 weight percent, can usually be tolerated without significant loss of selectivity, reactivity and stability.

Generally, the Direct Synthesis process is carried out batchwise in a slurry and the alcohol fed into the slurry as a gas or liquid. Gaseous introduction is preferred. An induction period lasting from a few minutes up to about five hours may be observed. The initial alcohol feed rate is optionally controlled at a low level and increased following the induction period. Similarly, the alcohol feed rate is optionally reduced after about 70 weight percent silicon conversion to minimize the formation of tetraalkoxysilanes. Generally, once the reaction is running, the alcohol feed rate can be adjusted to provide the desired level of alcohol conversion. One skilled in the art can readily adjust the feed rate in a given reaction run by monitoring the product composition. If the feed rate is too high the product stream will contain a larger proportion of unreacted alcohol.

E. Solvent for the Direct Synthesis

Solvents for the slurry-phase Direct Synthesis process of trialkoxysilanes maintain the copper-activated silicon in a well-dispersed state and facilitate both mass transfer of the alcohol to catalytic sites and heat transfer between the reacting solids and the reactor. Solvents useful in the process of this invention are thermally stable compounds or mixtures that do not degrade under the activation and reaction conditions. Structurally, such solvents can be linear or branched paraffins, naphthenes, alkylated benzenes, aromatic ethers, polyaromatic hydrocarbons, and the like. In the latter case, the aromatic rings can be fused together as in naphthalene, phenanthrene, anthracene and fluorene derivatives. They can be joined by single carbon-carbon bonds as in biphenyl and terphenyl derivatives, or they can be joined by bridging alkyl groups as in the diphenylethanes and tetraphenylbutanes. One class of preferred solvents is the high temperature stable organic solvents typically used as heat exchange media. Examples include THERMINOL® 59, THERMINOL® 60, THERMINOL® 66, DOWTHERM® HT, MARLOTHERM® S, MARLOTHERM® L, diphenyl ether, diphenyl and terphenyl and their alkylated derivatives with normal boiling points higher than about 250° C.

THERMINOL® is the Monsanto Company trade name for heat transfer fluids. THERMINOL® 59 is a mixture of alkyl-substituted aromatic compounds recommended for use between −45 to 315° C. THERMINOL® 60 is a mixture of polyaromatic compounds with an average molecular weight of 250. Its optimum temperature range is from −45° to 315° C. THERMINOL® 66 and DOWTHERM® HT are mixtures of hydrogenated terphenyls with an average molecular weight of 240. Maximum temperature limit is about 370° C. THERMINOL® 59, THERMINOL® 66 and DOWTHERM® HT are preferred solvents of this invention. DOWTHERM® fluids are produced by Dow Chemical Company.

MARLOTHERM® is the Hüls AG trade name for its heat transfer fluids. MARLOTHERM® S is a mixture of isomeric dibenzylbenzenes. MARLOTHERM® L is a mixture of isomeric benzyl toluenes. Both can be used at temperatures up to about 350° C. Both are preferred solvents for the instant invention.

Suitable alkylated benzenes for the practice of the instant Direct Synthesis process are dodecylbenzene, tridecylbenzene, tetradecylbenzene and their mixtures such as are sold by Vista Chemical Company under the trade name NALKYLENE®, and by Condea Augusta s.p.a. under the trade names ISORCHEM® and SIRENE®. NALKYLENE® 550BL, NALKYLENE® 550L, NALKYLENE® 500, NALKYLENE® 501, NALKYLENE® 600L and NALKYLENE® V-7050 are particularly preferred reaction solvents for use with the nanosized CuCl precursors. With nanosized copper and nanosized copper oxides, the alkylated benzene solvents afford better reaction stability and selectivity to the trialkoxysilanes when used at temperatures between 180-220° C.

Naphthenes are cycloparaffins. They are components of white mineral oils, petroleum distillates and some fuels. White mineral oils and petroleum distillates also contain normal and branched paraffins (see A. Debska-Chwaja, et al., *Soap, Cosmetics and Chemical Specialties*, (Nov. 1994), pp 48-52; ibid., (March 1995) pp64-70). Suitable examples of commercial products containing naphthenes and paraffins and useful as reaction solvents for this invention are the white mineral oils, CARNATION 70, KAYDOL, LP-100 and LP-350, and the petroleum distillates, PD-23, PD-25 and PD-28, all of which are sold by Crompton Corporation under the WITCO trade name. Other examples of naphthenes useful as reaction solvents are butylcyclohexane, decahydronaphthalene, perhydroanthracene, perhydrophenanthrene, perhydrofluorene and their alkylated derivatives, bicyclohexyl, perhydroterphenyl, perhydrobinaphthyl and their alkylated derivatives.

Mixtures of alkylated benzenes, naphthenes and normal and branched paraffins with polyaromatic hydrocarbons are also useful as reaction solvents for the instant invention.

Used solvents can be treated with boric acid and borates as described in U.S. Pat. No. 5,166,384, or formic acid as disclosed in U.S. Pat. No. 6,090,965, or by thermal hydrolysis as disclosed in U.S. Pat. No. 6,166,237 and reused in subsequent trialkoxysilane Direct Synthesis reactions. These disclosures are incorporated in their entirety by reference herein.

Silicon metal, copper catalyst precursor, promoter and solvent can be added together in the reactor in any order. The solvent is present in an amount sufficient to disperse the solid and gaseous reactants homogeneously. Generally, reactions are initiated with solvent and solids in a gravimetric ratio between about 1:2 and about 4:1, preferably about 1:1 to about 2:1. However, as the silicon is consumed during batchwise Direct Synthesis, the solvent-to-solids ratio will increase. The ratio can be maintained within narrow limits of the preferred range for continuous reactions.

F. Copper-Silicon Activation Conditions

Activation is the process of incorporating catalyst, and if desired, other auxiliary agents, into the silicon metal reactant to make it reactive with the alcohol. Activation may be performed in the same reactor used for the Direct Synthesis or in a separate reactor. In the latter case, the activated silicon is typically and desirably transported to the synthesis reactor in an anhydrous, non-oxidizing atmosphere. Transportation of the activated silicon as a slurry in the reaction solvent is especially preferred.

Activation of copper catalyst precursors and silicon in a slurry reactor can generally be performed at about 20-400° C., preferably between about 150-300° C., with mixtures containing from about 0.01-50 weight percent copper relative to silicon. The phosphorus-containing promoter is optionally present during the activation. In one embodiment, the agitated slurry is heated to about 200-300° C. in an inert gas (for example, nitrogen or argon) atmosphere for about 0.01-24 hours prior to the injection of the alcohol reactant. Time and temperature must be sufficient to bring about effective copper-silicon activation and avoid significant loss of trialkoxysilane selectivity, and/or formation of hydrocarbons and water during the Direct Synthesis. It is not necessary that all of the silicon be present during the activation step. For example, a portion of the silicon to be used and all of the copper catalyst precursor can be activated in the reaction solvent and the remaining silicon added thereafter.

Alternatively, alcohol, optionally admixed with inert gas, is introduced into the agitated slurry of copper catalyst precursor, promoter, silicon and reaction solvent during heating. Reaction ensues beyond some minimum temperature, typically greater than 180° C., at atmospheric pressure. Preferably, alcohol vapor is introduced into an agitated slurry after the temperature is greater than or equal to about 180° C.

Activation of mixtures comprising silicon and copper catalyst precursors can produce water, aldehydes, carbon monoxide, HCl, silicon tetrachloride and other compounds, depending on the specific copper catalyst precursor charged. These compounds are preferably volatilized and absent prior to the start of the Direct Synthesis of the trialkoxysilanes. If they are present in the synthesis reactor or in the product retention vessel, they can contribute to gel formation, poor reaction selectivity and reduced trialkoxysilane recovery. When CuCl or other halogen-containing copper precursor is used, provision must be made to protect the reactor and ancilliary equipment from corrosion.

G. Reaction Conditions

Designs, descriptions and operational considerations pertinent to three phase reactors are contained in the following monograph, articles and patents:

A. Ramachandran and R. V. Chaudhari, *Three Phase Catalytic Reactors*, Gordon and Breach Science Publishers, NY, 1983

N. Gartsman, et al., *International Chemical Engineering*, vol. 17 (1977) pp 697-702

H. Ying, et al., *Industrial & Engineering Chemistry, Process Design & Development*, vol. 19 (1980) pp 635-638

N. Satterfield, et al., *Chemical Engineering Science*, vol. 35 (1980) pp 195-202

M. Boxall, et al., *Journal of Metals*, (August 1984) pp 58-61

US. Pat. No. 4,328,175

Reactors may be operated in a batchwise, semi-continuous or continuous mode. In batchwise operation, a single addition of silicon and copper catalyst is made to the reactor at the outset and alcohol is added continuously, or intermittently, until the silicon is fully reacted, or reacted to a desired degree of conversion. In continuous operation, silicon and copper catalyst are added to the reactor initially and thereafter to maintain the solids content of the slurry within desired limits. The batchwise mode is illustrated in U.S. Pat. No. 4,727,173 and the continuous mode in U.S. Pat. No. 5,084,590. Both of these patents are incorporated in their entirety by reference herein.

In its preferred form in accordance with the present invention, the Direct Synthesis of trialkoxysilanes is conducted in a continuously agitated slurry reactor containing thermally stable solvent, silicon, copper catalyst precursor, phosphorus-containing promoter and foam control agents in contact with alcohol vapor. The number and type of impellers are selected to afford effective solids suspension, gas dispersion and mass transfer of alcohol to the copper-activated silicon. The reactor may have a single nozzle or multiple nozzles for the introduction of gaseous alcohol. A means of continuous or intermittent addition of promoter, copper catalyst precursor-silicon mixture, or of silicon, is also provided. Means for continuous removal and recovery of the volatile reaction products and unreacted alcohol are also desirably provided. Separation and purification of the trialkoxysilane products are optimally performed in the manner disclosed in U.S. Pat. Nos. 4,761,492 or 4,999,446, the contents of both of which are incorporated in their entirety by reference herein.

When the initial loading of silicon and copper catalyst precursor is activated according to the method of the instant invention, continuous slurry phase Direct Synthesis of trialkoxysilanes is advantageously continued by adding only silicon, or silicon containing less copper catalyst precursor and phosphorus-containing promoter than that initially added. In this way, the copper concentration of the slurry is controlled to minimize the transformation of the alcohol to hydrocarbons and water (Equations 3 and 5 above). Disadvantages caused by water have been recited hereinabove.

The reaction is generally conducted at temperatures above about 150° C., but below such a temperature as would degrade or decompose the reactants, promoter, solvents or desired products. Preferably, the reaction temperature is maintained in a range from about 200° C. to about 280° C. The reaction of methanol with the copper-activated silicon of the present invention is preferably operated at about 220-270° C., and most preferably at about 230-260° C., whereas the reaction of ethanol is preferably operated at about 200-240° C., and most preferably at about 205-230° C. The pressure at which the reaction is conducted can be varied from subatmospheric to superatmospheric. Atmospheric pressure is generally employed in the reaction of methanol with copper-activated silicon. Pressures in the range of about 1-5 atmospheres are advantageous to rate and trialkoxysilane selectivity in the Direct Synthesis process herein.

Preferably, the contents of the reaction mixture are agitated to maintain a well-mixed slurry of the copper-activated silicon particles, promoter and gaseous alcohol in the solvent. The exit line carrying the gaseous reaction mixture from the reactor is preferably well insulated to insure that the trialkoxysilane does not reflux. Refluxing can encourage the consecutive reaction of the trialkoxysilane with the alcohol, resulting in loss of the desired trialkoxysilane product by the formation of the tetraalkoxysilane.

The presence of gaseous alcohol, hydrogen gas and other gases in the reactor can occasionally lead to foaming. This is undesirable since it can result in loss of solvent, promoter and copper-activated silicon from the reactor. U.S. Pat. No. 5,783,720 indicates that the addition of foam control agents, preferably silicon-containing foam control agents such as OSi Specialties SAG® 1000, SAG® 100, SAG® 47, Wacker-Chemie OEL AF 98/300 and Dow Corning FS 1265, will negate or control this problem. SAG® 1000, SAG® 100 and SAG® 47 are compositions comprising polydimethyl-silicones and silica. FS 1265 and OEL AF 98/300 contain fluorinated silicones, for example, poly(trifluoropropylmethylsiloxanes). The foam control agent must be durable such that a single addition at the outset of a batch reaction is sufficient to avoid or mitigate foam formation until all of the silicon has been consumed.

At constant temperature, the reaction rate depends critically on the surface area and particle size of the silicon and copper catalyst precursor and on the feed rate of the alcohol. Higher reaction rates are obtained at higher surface areas, finer particle sizes and higher alcohol feed rates. These parameters are selected so that a safe, economically sustainable product output is realized without endangerment to people, property and the environment. Deactivation can be reduced or forestalled and stability sustained by reducing the alcohol flow during the course of a triethoxysilane Direct Synthesis. This control not only decreases the excess alcohol available for dehydrogenation and other side reactions, it also facilitates product separation in the stripping column downstream of the reactor.

High selectivity to trialkoxysilanes, high reaction rates and stable performance are realized when copper catalyst precursors and phosphorus-containing promoters are used in the present invention. This is particularly so when trimethoxysilane is prepared by the Direct Synthesis process of the instant invention. Preferably, the copper catalyst precursor is a copper (II) hydroxide with surface area greater than 20 square meters per gram containing 1.5-4.5 weight percent phosphate as promoter. By the teachings of this invention, the trialkoxysilane/tetraalkoxysilane gravimetric ratio is at least 15, preferably greater than 17 and most preferably greater than 20. Simultaneously, silicon conversion is greater than 60 percent, preferably greater than 70 percent and most preferably greater than 85 percent before the reaction rate and/or selectivity to trialkoxysilane falls to unacceptable levels. All of these features of the instant invention will be illustrated hereinunder by example.

EXAMPLES

The following Examples illustrate the preferred embodiments of the instant invention. These are not intended to limit the scope of the invention. Rather, they are presented merely to facilitate the practice of the invention by those of ordinary skill in the art.

(1) Abbreviations and Units Used

Abbreviations used in the presentation of the data of the illustrative examples are the following:

1.27 cm wide baffles were affixed to the wall of the reactor. Agitation was provided by two impellers attached to an axial shaft. The bottom one was a six-blade Rushton turbine, 9.5 cm in diameter. A three-blade marine propeller of the same diameter was placed 10 cm above the turbine. A variable speed supplied power for agitation. An electric heating mantle controlled by a heater/temperature controller was used to heat the reactor. Valved connections were available at the top of the reactor for the attachment of stainless steel cylinders, which could be used for the injection of additives (under nitrogen pressure) into the reactor, or sampling the reactor contents.

Methanol or ethanol was supplied to the reactor from a 1 L storage container via a calibrated FMI laboratory pump. Coiled stainless steel tubing, 0.32 cm internal diameter×305 cm length, placed in a 4 L silicone oil bath controlled at about 160° C. served as the alcohol vaporizer. The alcohol inlet line entered through the top of the reactor. It was heat traced and controlled at 120° C. to prevent condensation of the vapor. Alcohol vapor was injected 2.5 cm from the bottom of the reactor and below the level of the six-blade turbine through a single downward pointing (0.63 cm internal diameter) sparger. A pressure gauge attached to the alcohol vapor inlet line gave higher readings when the sparger was plugged. Additional alcohol was supplied to the storage container during an experiment to maintain an uninterrupted flow of this reagent.

Reaction products and unreacted alcohol exited the reactor through a 76 cm×3.8 cm internal diameter packed tube, which served as entrainment separator and partial distillation column to remove solvent and higher boiling silicates from the product stream. The packing was ceramic saddles and stainless steel mesh. Five thermocouples were distributed along the length of the tube to record temperatures and indicate foaming. The lowest thermocouple was flush with the top of the reactor. As was indicated hereinabove, foaming was controlled by the use of FS 1265, AF 98/300 and SAG® 100. Flexible tubing connected the outlet of the entrainment separator/partial distillation column to the four-way valve regulating sampling and crude product flow to the distillation columns.

Two ten plate Oldershaw distillation columns served to separate the liquid reaction products and unreacted alcohol from the gases. Effluent from the reactor was admitted into the top trays of the lower column, which was attached to a 3 neck 5 L round bottom flask supported in a heating mantle. A

| ABBREVIATION | MEANING | ABBREVIATION | MEANING |
|---|---|---|---|
| TMS | $HSi(OCH_3)_3$ | g | gram |
| TMOS | $Si(OCH_3)_4$ | kg | kilogram |
| MeOH | $CH_3OH$ | L | liter |
| SEL | $HSi(OR)_3/Si(OR)_4$ | nm | nanometer |
| min | minute | μ | micron |
| % Si/hr | Percent silicon converted per hour | $m^2/g$ | square meters per gram |
| wt % | weight percent | rpm | revolutions per minute |
| TH59 | THERMINOL® 59 | $cm^{-1}$ | Wavenumber |
| ppm | Parts per million | Conv | Conversion |
| mL | Milliliter | | |

(2) Equipment Used

An 8 liter three-phase stainless steel slurry reactor was used for the illustrative Examples presented here. Four 90° spaced, magnetically controlled reflux condenser and distillation head with thermocouple capped the upper column. The reflux condenser and another condenser downstream were cooled to −25° C. by circulating silicone oil. Uncondensed gases exited the condenser through a vapor lock bubbler into the hood. Wider tubing was employed downstream of the bubbler to avoid backpressures likely to shatter the glassware (columns, condensers and bubbler) or cause leaks at the joints. A gas sampling port was provided at a T joint downstream of the bubbler. Effluent gas flow was diluted with nitrogen prior to its discharge into the laboratory hood. A thermocouple was located in the second opening of the three-neck flask and the intake to an FMI laboratory pump in the other. The pump was used to transfer liquid product from the flask to Teflon coated polyethylene storage bottles. All glass containers used to store or sample trimethoxysilane and triethoxysilane were washed with dilute HCl, rinsed thoroughly with methanol (or ethanol) and oven dried at 110° C. prior to use.

Gas chromatographic analysis of the reaction product was performed as described below.

(3) General Copper Silicon Activation and Reaction Procedure

Typically, the reactor was charged with solvent, silicon, copper catalyst precursor and foam control agent and then sealed. The solvent to silicon ratio was typically 2:1 or 4:1. The slurry was agitated at 670-900 rpm and nitrogen introduced during heating to the desired reaction temperature. Simultaneously, the alcohol vaporizer and feed inlet were heated to 150-170° C. and the refrigerant circulated through the reflux condenser was cooled to ~−25° C. Alcohol flow to the reactor was initiated when all the set temperatures were attained. Nitrogen flow was reduced to ~50 ml/min during the reaction.

Once the alcohol flow was underway, sampling and analysis of the vent gas stream for hydrogen were done every 10-30 minutes until a stable composition was established. That indicated the end of the induction period. Thereafter, gas sampling was done every 30 minutes to monitor hydrogen and other uncondensed byproducts. During the course of the reaction, total vent gas flow was used as an approximate measure of the reaction rate according to the stoichiometry of equation (1).

Samples were collected in previously acid washed, alcohol rinsed, oven-dried containers attached at the four-way sampling valve for 2-5 minutes every half hour. The containers were cooled in dry-ice during sample collection. Samples were weighed and analyzed by gas chromatography. The bulk of the liquid product was condensed in the three-neck flask, which served as the reboiler and transferred to storage. All of these data were used to calculate the temporal composition of the product stream, its selectivity to trialkoxysilane, the reaction rate and overall silicon conversion. Usually, reactions were terminated after >85 % of the silicon charged to the reactor had been reacted. In some cases, terminations were made at lower and higher silicon conversions depending on the objective of the experiment. Residual solids from the reaction were sometimes recovered and weighed to calculate silicon conversion.

Gas samples were analyzed for hydrogen, nitrogen and hydrocarbon (e.g. methane, ethane) content on a Hewlett Packard 5840 gas chromatograph fitted with a GS-Molesieve 30 m×0.53 mm internal diameter (J & W Scientific, Folsom, Calif.) capillary column and flame ionization detector. Argon was the carrier gas. Gas chromatography-mass spectrometry was used to analyze for dimethyl ether. Liquid samples containing alkoxysilanes were analyzed on a Hewlett Packard 5890 gas chromatograph fitted with a 3.66 m×3.18 mm internal diameter stainless steel 20% OV-101 on 60/80 mesh Chromosorb WHP column (Supelco Inc., Bellafonte, Pa.) and thermal conductivity detector. Helium was the carrier gas.

(4) Materials Used

Technical grade silicon samples utilized in the experiments of the illustrative Examples are identified in Table 2 along with relevant analytical data. Particles in the size range, 45-300 micrometers, accounted for approximately 70 weight percent of the silicon. THERMINOL® 59 was the only solvent used. FS 1265 (Dow Corning) and SAG® 47 were the foam control agents. Methanol was ACS grade (>99.9 wt %) with water content <0.1 wt %

TABLE 2

COMPOSITION OF SILICON USED IN THE EXAMPLES

| ELEMENT | VALUE |
|---|---|
| Al, wt % | 0.2 |
| Ba, ppm | 13.4 |
| Ca, ppm | 517 |
| Cr, ppm | 28.6 |
| Cu, ppm | 19.5 |
| Fe, wt % | 0.39 |
| Mg, ppm | 23.9 |
| Mn, ppm | 125 |
| Ni, ppm | <10 |
| P, ppm | 25 |
| Pb, ppm | <10 |
| Sn, ppm | <10 |
| Ti, ppm | 312 |
| V, ppm | 20.5 |
| Zn, ppm | 6.6 |
| Zr, ppm | 100 |

Copper hydroxide from various suppliers was tested. Identification and descriptions are provided in the examples below. The copper phosphates used are similarly described.

(5) Examples 1-21

Examples 1-21 illustrate that all copper hydroxides are not equally or acceptably effective in the Direct Synthesis of trimethoxysilane.

The sources of copper hydroxide are identified in Table 3. Direct Syntheses of trimethoxysilane were performed at 250° C. in the 8 liter reactor using the activation and reaction procedure described hereinabove. Each experiment required 3.5 kg THERMINOL® 59, 1.75 kg silicon, 13.2 g copper hydroxide, 5.0 g fluorosilicone defoamer and 8.95 g/min methanol. (Example 20 was run with 11 g/min methanol).

TABLE 3

PERFORMANCE OF $Cu(OH)_2$ FROM GRIFFIN, PHIBROTECH, SULCOSA, SALDECO, CUPROQUIM, SPIESS-URANIA AND JOHNSON MATTHEY IN SINGLE BATCH DIRECT SYNTHESIS OF $HSi(OCH_3)_3$

| SUPPLIER/EXAMPLE | Si CONV., % | TMS, wt % | TMOS, wt % | AVG. RATE, % Si/h | SEL |
|---|---|---|---|---|---|
| GRIFFIN | | | | | |
| Example 1 | 71.24 | 91.13 | 3.59 | 7.77 | 25.39 |
| Example 2 | 88.95 | 92.35 | 4.04 | 6.24 | 22.86 |
| Example 3 | 87.89 | 82.17 | 13.33 | 7.03 | 6.17 |
| Example 4 | 87.24 | 86.16 | 11.85 | 6.27 | 7.27 |
| Example 5 | 90.76 | 89.87 | 7.59 | 6.33 | 11.84 |

TABLE 3-continued

PERFORMANCE OF Cu(OH)₂ FROM GRIFFIN, PHIBROTECH, SULCOSA, SALDECO, CUPROQUIM, SPIESS-URANIA AND JOHNSON MATTHEY IN SINGLE BATCH DIRECT SYNTHESIS OF HSi(OCH₃)₃

| SUPPLIER/EXAMPLE | Si CONV., % | TMS, wt % | TMOS, wt % | AVG. RATE, % Si/h | SEL |
|---|---|---|---|---|---|
| PHIBROTECH | | | | | |
| Example 6 | 88.95 | 92.49 | 4.72 | 6.35 | 19.60 |
| Example 7 | 86.25 | 91.82 | 6.11 | 6.68 | 15.02 |
| Example 8 | 87.19 | 91.22 | 6.12 | 6.38 | 14.91 |
| SULCOSA | | | | | |
| Example 9 | 88.87 | 89.45 | 4.95 | 7.94 | 18.07 |
| Example 10 | 79.16 | 90.15 | 4.49 | 8.05 | 20.08 |
| Example 11 | 84.04 | 89.93 | 4.81 | 7.94 | 18.68 |
| Example 12 | 59.99 | 83.62 | 12.66 | 7.35 | 6.61 |
| Example 13 | 54.91 | 83.09 | 13.42 | 7.32 | 6.19 |
| SALDECO | | | | | |
| Example 14 | 89.35 | 85.80 | 9.89 | 7.10 | 8.67 |
| CUPROQUIM | | | | | |
| Example 15 | 48.59 | 90.99 | 8.27 | 6.07 | 11.00 |
| SPIESS-URANIA | | | | | |
| Example 16 | 75.35 | 90.27 | 6.46 | 6.70 | 13.96 |
| JOHNSON-MATTHEY | | | | | |
| Example 17 | 75.57 | 90.65 | 4.18 | 7.49 | 21.69 |
| Example 18 | 72.67 | 90.04 | 4.15 | 7.27 | 21.72 |
| Example 19 | 71.32 | 89.47 | 4.99 | 7.07 | 17.92 |
| Example 20 | 76.86 | 87.10 | 6.61 | 9.41 | 13.17 |
| Example 21 | 73.22 | 90.09 | 4.50 | 7.57 | 20.01 |

The data show that eleven of the twenty-one copper hydroxide samples tested yielded crude trimethoxysilane product containing greater than 6 weight percent TMOS in single batchwise reactions. Copper hydroxides affording less than 6 weight percent TMOS (Examples 1, 2, 6, 9, 10, 11, 17, 18, 19, 21) were not confined to a single supplier.

TMS is formed via the secondary reaction of TMS with methanol (see equation [2] above). In the experiments with unacceptable copper hydroxides (Examples 3, 4, 5, 7, 8, 12-16, 20), its formation generally exceeded 10 weight percent between 1-20 percent silicon conversion, but decreased thereafter to 4-9 wt %. With the copper hydroxides affording <6 wt % TMOS in the total product mixture (Examples 1, 2, 6, 9, 10, 11, 17, 18, 19, 21), TMOS was always <9 wt % between 1-20 percent silicon conversion, and was 2-5 wt % later on. Thus, there might be one or more constituents in an acceptable Cu(OH)₂, or one or more agents absent from said Cu(OH)₂, which influence the transformation of TMS to TMOS.

(6) Examples 22-31

Examples 22-31 illustrate that copper hydroxides, which yield acceptable performance in a single batch experiment do not necessarily maintain this performance when multiple silicon charges are made to the reactor during semi-continuous or multibatch operation.

Each example consists of two or more batch reactions conducted in a single solvent charge. The first batch reaction (designated A in each example) was run up to about 60-90 percent silicon conversion with the material quantities and conditions disclosed in Examples 1-21 above according to the operations described in the general procedure. Thereafter, silicon and copper hydroxide were recharged to the residual reaction slurry so that initial weight of silicon for the second reaction was 1750 g. The weight ratio of copper hydroxide to silicon in the recharge was maintained at 0.00754. The third and subsequent batch reactions were performed in the same manner.

Table 4 lists the copper hydroxides used and, where applicable, shows the correspondence between them and those used in Examples 1-21. Methanol flow rate was 8.95 g/min, except in Example 27 in which it was 7 g/min.

TABLE 4

Cu(OH)₂ USED IN EXAMPLES 1-21 AND EXAMPLES 22-32

| Cu(OH)₂ SUPPLIER | EXAMPLE 1-21 | EXAMPLE 22-32 |
|---|---|---|
| PHIBROTECH | Example 6, | Example 24 |
| GRIFFIN | Example 1 | Example 31 |
| | | Example 30 |
| SULCOSA | Example 10 | Example 25 |
| | | Example 26 |
| | | Example 27 |
| JOHNSON-MATTHEY | Example 17 | Example 28 |
| | Example 19 | Example 29 |
| | | Example 22 |
| | | Example 23 |

TABLE 5

PERFORMANCE OF Cu(OH)₂ FROM VARIOUS SOURCES IN MULTIBATCH DIRECT SYNTHESIS OF HSi(OCH₃)₃

| EXAMPLE | Si CONV., % | TMS, wt % | TMOS, wt % | AVG. RATE, % Si/h | SEL |
|---|---|---|---|---|---|
| 22A | 75.75 | 89.62 | 5.04 | 7.57 | 17.80 |
| 22B | 65.63 | 88.74 | 6.28 | 7.03 | 14.13 |
| 23A | 73.22 | 90.09 | 4.50 | 7.57 | 20.01 |
| 23B | 65.86 | 88.36 | 6.25 | 6.93 | 14.14 |
| 24A | 87.79 | 91.18 | 4.85 | 6.75 | 18.81 |
| 24B | 71.45 | 89.32 | 5.81 | 6.86 | 15.38 |
| 24C | 54.53 | 87.94 | 7.40 | 5.04 | 11.88 |
| 25A | 75.48 | 89.81 | 4.65 | 8.23 | 19.30 |
| 25B | 68.36 | 88.52 | 6.09 | 8.04 | 14.54 |
| 25C | 70.65 | 85.79 | 9.12 | 7.64 | 9.40 |
| 26A | 73.16 | 88.66 | 5.49 | 8.13 | 16.14 |
| 26B | 73.28 | 87.90 | 6.66 | 8.14 | 13.21 |
| 26C | 61.95 | 87.20 | 7.37 | 7.99 | 11.83 |
| 27A | 76.48 | 93.62 | 4.05 | 5.88 | 23.12 |
| 27B | 87.85 | 93.15 | 4.82 | 6.27 | 19.33 |
| 27C | 79.86 | 91.70 | 6.26 | 5.88 | 14.65 |
| 28A | 75.57 | 90.65 | 4.18 | 7.49 | 21.69 |
| 28B | 69.88 | 89.98 | 4.58 | 7.55 | 19.64 |
| 28C | 59.13 | 88.01 | 7.41 | 6.57 | 11.87 |
| 29A | 71.32 | 89.47 | 4.99 | 7.07 | 17.92 |
| 29B | 71.46 | 90.25 | 5.02 | 7.15 | 17.99 |
| 29C | 54.61 | 89.25 | 6.81 | 6.24 | 13.11 |
| 30A | 81.01 | 89.82 | 4.55 | 7.84 | 19.72 |
| 30B | 80.12 | 89.19 | 5.17 | 8.57 | 17.26 |
| 30C | 63.08 | 88.97 | 5.26 | 7.88 | 16.93 |
| 31A | 71.24 | 91.13 | 3.59 | 7.77 | 25.39 |
| 31B | 76.93 | 92.01 | 4.42 | 7.84 | 20.84 |
| 31C | 71.31 | 89.43 | 5.35 | 8.23 | 16.72 |
| 31D | 69.10 | 88.69 | 6.26 | 7.90 | 14.17 |

In general, TMOS increased as the number of silicon charges was increased. TMOS exceeded 6 wt % in the second charge of Examples 22, 23, 25 and 26 and in the third charge of Examples 24, 27, 28 and 29. At least 3 silicon charges could be made with the copper hydroxides used in the experiments of Examples 30 and 31 before TMOS exceeded 6 wt %. Whereas the copper hydroxides used in Examples 6, 10, 17 and 19 gave acceptable performance in single batch operation, their performance was unacceptable when two or more batch reactions (Examples 24, 25, 28 and 29) were run. There appears to be some compositional, structural or morphological property, which distinguishes the copper hydroxides affording acceptable performance from those which do not.

(7) Examples 32A-32E

These Examples illustrate that the performance of an unacceptable copper hydroxide can be improved when it is mixed with one yielding <6 wt % TMOS.

The Direct Synthesis experiments were performed with a SULCOSA copper hydroxide, which gave 11-14 wt % TMOS between 1-20% Si conversion in single batch reactions (Example 32A) and one from GRIFFIN (Example 32E), which gave <5 wt % TMOS in the same silicon conversion range. The weights of the copper hydroxides used in the experiments are listed in Table 6. The experiments were done as described hereinabove for Examples 1-20. A summary of the results of the five experiments is set forth below.

Copper hydroxides used in Examples 1-31 were analyzed for copper content, water content, trace metals, sulfate, phosphate, chloride, surface area and particle size. All had surface areas >10 m$^2$/g and average particle size <5 microns. Chloride was less than 10 ppm in all except that used in Example 14. Copper content ranged 56-62 wt %, but this variation was determined not to be the critical performance variable. Water content (weight loss up to 250° C.) and trace metals such as Al, Fe, Sn, Pb and Zn were all found to be within the acceptable limits specified hereinabove. Only the phosphate concentration was found to be a significant determinant and predictor of catalytic performance. The presence of phosphates in the copper hydroxides was indicated by FTIR. The spectra showed bands in the 900-1150 cm$^{-1}$ region. Phosphate concentration was measured either as phosphorus by inductively coupled plasma spectroscopy or as phosphomolybdate by visible spectrophotometry. Table 7 summarizes the analytical data, which underpins the correlation of phos-

TABLE 6

TMOS DATA FOR EXAMPLES 32A-32E

| EXAMPLE 32A 13.2 g Sulcosa Cu(OH)$_2$ | | EXAMPLE 32B 11.88 g Sulcosa, 1.32 g Griffin Cu(OH)$_2$ | | EXAMPLE 32C 9.9 g Sulcosa, 3.3 g Griffin Cu(OH)$_2$ | |
|---|---|---|---|---|---|
| Si Conv, % | TMOS, wt % | Si Conv, % | TMOS, wt % | Si Conv, % | TMOS, wt % |
| 3.20 | 13.43 | 3.04 | 13.83 | 3.19 | 11.87 |
| 6.95 | 12.57 | 6.87 | 9.20 | 6.99 | 7.80 |
| 10.87 | 12.15 | 10.90 | 7.05 | 11.15 | 6.94 |
| 14.95 | 11.72 | 15.14 | 6.45 | 15.39 | 6.26 |
| 19.06 | 11.71 | 19.45 | 6.07 | 19.66 | 5.71 |

| EXAMPLE 32D 1.32 g Sulcosa, 11.88 g Griffin Cu(OH)$_2$ | | EXAMPLE 32E 13.2 g Griffin Cu(OH)$_2$ | |
|---|---|---|---|
| Si Conv, % | TMOS, wt % | Si Conv, % | TMOS, wt % |
| 3.03 | 1.61 | 3.43 | 1.89 |
| 7.03 | 1.97 | 5.23 | 2.85 |
| 9.14 | 2.18 | 11.27 | 3.04 |
| 16.11 | 3.24 | 17.83 | 2.80 |
| 19.84 | 3.49 | 19.36 | 2.93 |

Note that in Example 32B, with only 10% of the Griffin copper hydroxide, TMOS was formed at approximately 6 wt % of the product mixture after about 20 percent silicon conversion. The improvement was more marked in Example 32C. In contrast, 10 wt % of a Sulcosa Cu(OH)$_2$ had no negative effect on the performance of the Griffin material (Example 32D). Thus, the particular Griffin Cu(OH)$_2$ used contained a desirable constituent, which was absent from the Sulcosa Cu(OH)$_2$ and which is effective at relatively low levels in reducing TMOS formation in the early stages of the Direct TMS Synthesis.

(8) Examples 33-42

These examples show that phosphate content is a critical feature distinguishing copper hydroxides affording acceptable performance in the Direct Synthesis of trimethoxysilane from those, which do not. Acceptable performance, as defined hereinabove, means TMS>88 wt %, TMOS<6 wt % after silicon conversions >50% in single batch and multibatch operations.

phate concentration of copper hydroxide with acceptable performance in the Direct Synthesis of trimethoxysilane.

The data of Examples 33 and 34 show that the GRIFFIN copper hydroxides used in the experiments of Examples 1, 30 and 31 contained 3.5-4.5 wt % phosphate (equivalent to 7-9 wt % copper orthophosphate). This level of phosphate facilitated satisfactory catalytic performance in single batch and multibatch operation of the Direct Synthesis of trimethoxysilane. Examples 35-37 show that the phosphate concentrations of the SULCOSA copper hydroxides used in the experiments of Examples 10, 25, 26 and 27 were all less than 0.05 wt %. In this range, TMOS can be less than 6 wt % in single batch reactions, but it will exceed this criterion when two or more batch reactions are run in succession. Examples 38-42 show that the phosphate concentration in the JOHNSON MATTHEY copper hydroxides used in the experiments of Examples 17-19, 21, 22, 28 and 29 was in the range 1.2-3.5 wt % (equivalent to 2.4-7 wt % copper orthophosphate). In conjunction with the data of Examples 33 and 34, it can be concluded that phosphate concentrations from about 1.2 to about 4.5 weight percent will afford TMOS<6 wt % in single and multibatch reactions.

TABLE 7

P, $PO_4^{3-}$ AND $Cu_3(PO_4)_2$ CONTENT OF VARIOUS $Cu(OH)_2$ SAMPLES

| EX-AMPLE | $Cu(OH)_2$ SOURCE | USED IN EXAMPLES | P, wt % | $PO_4^{3-}$, wt % | $Cu_3(PO_4)_2$, wt % |
|---|---|---|---|---|---|
| 33 | GRIFFIN | 30 | 1.22 | 3.74 | 7.49 |
| 34 | | 1, 31, 32B-E | 1.34 | 4.11 | 8.23 |
| 35 | SULCOSA | 10, 25 | 0.0058 | 0.018 | 0.036 |
| 36 | | 27 | 0.0099 | 0.030 | 0.061 |
| 37 | | 26 | 0.0104 | 0.032 | 0.064 |
| 38 | JOHNSON-MATTHEY | 19, 29 | | 1.29 | 2.58 |
| 39 | | 22 | | 1.80 | 3.61 |
| 40 | | 21 | | 2.20 | 4.41 |
| 41 | | 18 | | 3.25 | 6.51 |
| 42 | | 17, 28 | | 3.28 | 6.57 |

(9) Examples 43A-43G

These Examples illustrate the beneficial effect of adding basic copper phosphate to improve the reaction performance and control tetramethoxysilane (TMOS) formation in the Direct Synthesis of trimethoxysilane.

Seven separate batch experiments are summarized in this example. Basic copper phosphate ($Cu_3(PO_4)_2 \cdot Cu(OH)_2$, Aldrich) was added to the reaction slurry, or to the SULCOSA copper hydroxide prior to its addition to the reactor. The SULCOSA copper hydroxide contained 0.025 wt % phosphate (equivalent to 0.050 wt % copper orthophosphate). Basic copper phosphate addition spanned the range, 1-16 weight percent, based on the weight of copper hydroxide charged. All other preset reaction conditions were unchanged from those disclosed in Examples 1-21.

The data (Table 8) show reduction in TMOS formation when basic copper phosphate was added to the reaction at between 2-16 weight percent of the copper hydroxide used. TMOS was less than about 5 wt % when the copper phosphate was 2-11 wt % of the copper hydroxide.

TABLE 8

REDUCING TMOS FORMATION WITH BASIC COPPER PHOSPHATE

| EX-AMPLE | Added CuPhos, wt % | Si CONV., % | TMS, wt % | TMOS, wt % | AVG. RATE, % Si/h | SEL |
|---|---|---|---|---|---|---|
| 43A | 0 | 83.21 | 89.40 | 5.40 | 7.24 | 16.53 |
| 43B | 1.78 | 81.28 | 88.88 | 5.38 | 7.17 | 16.53 |
| 43C | 3.78 | 78.41 | 89.36 | 4.08 | 7.59 | 21.88 |
| 43D | 5.56 | 81.60 | 89.17 | 4.67 | 7.36 | 19.11 |
| 43E | 8.33 | 86.01 | 89.62 | 4.68 | 7.22 | 19.16 |
| 43F | 10.53 | 79.65 | 89.80 | 4.29 | 7.03 | 20.93 |
| 43G | 15.77 | 67.95 | 87.62 | 4.98 | 6.47 | 17.59 |

(10) Examples 44A-44C

These Examples illustrate the performance improvement realized with copper pyrophosphate. The copper pyrophosphate was synthesized by the reaction of 100 g sodium metaphosphate (0.327 mole $Na_3P_3O_9$, Aldrich) with 137 g copper sulphate pentahydrate (0.49 mole $CuSO_4 \cdot 5H_2O$) at 70° C. Both solids were dissolved separately in 1 liter of deionized, distilled water. The phosphate was added slowly to the stirred, heated copper sulphate solution. The solid was recovered by filtration and washed thoroughly with deionized, distilled water before drying in vacuo at 50° C. Analysis gave Cu=34.89±0.10 wt %, P=15.64 wt %. FTIR revealed a strong band at 1144 $cm^{-1}$ and one of medium intensity at 927 $cm^{-1}$. The Cu/P atom ratio 1.1 was in good agreement with the expected value of 1.0 for copper pyrophosphate. The x-ray diffraction powder pattern showed excellent agreement with that of an authentic sample of the pyrophosphate.

The control Direct TMS Synthesis with the SULCOSA copper hydroxide is shown as Example 44A. Example 44B was done with 13.2 g SULCOSA copper hydroxide and 0.52 g of the copper metaphosphate. Reaction was taken to 60.65 percent Si conversion. Example 44C was a continuation of Example 44B after 1050 g Si, 7.92 g SULCOSA copper hydroxide and 0.31 g copper metaphosphate had been recharged to the reactor. In both Examples 44B and 44C, copper metaphosphate was charged at approximately 4 weight percent of the copper hydroxide used. Data for the three experiments are summarized in Table 9.

The data of Example 44B show a reduction in TMOS and improved selectivity accompanying use of copper metaphosphate. The improvement was sustained when the reaction was continued in the experiment of Example 44C.

TABLE 9

REDUCING TMOS FORMATION WITH COPPER METAPHOSPHATE

| | EXAMPLE 44A | EXAMPLE 44B | EXAMPLE 44C |
|---|---|---|---|
| Si Conversion, % | 83.21 | 60.65 | 77.91 |
| TMS, wt % | 89.40 | 90.10 | 90.51 |
| TMOS, wt % | 5.40 | 3.81 | 3.92 |
| Average Rate, % Si/h | 7.24 | 7.58 | 7.60 |
| Selectivity | 16.53 | 23.91 | 23.08 |

(11) Examples 45-46

These Examples illustrate the use of basic copper phosphate to sustain production of <6 wt % TMOS in multibatch experiments.

Reaction conditions and raw material quantities were those disclosed in Examples 22-32 above. Example 45 summarizes a Direct trimethoxysilane Synthesis experiment, with a SULCOSA copper hydroxide ($PO_4^{3-}$=0.006 wt %), during which three silicon charges (Examples 45A -45C) were made. The same copper hydroxide was used in Example 46 along with 8.33 wt % basic copper phosphate (1.1 g per 13.2 g $Cu(OH)_2$). Five silicon charges (Examples 46A -46E) were possible. At the end of each batch, additions of silicon were made so that 1.75 kg Si was available for the start of the next batch reaction. The proportions of added copper hydroxide to silicon and copper phosphate to copper hydroxide were kept constant. Results are set forth in Tables 10 and 11.

The basic copper phosphate was prepared by the reaction of aqueous solutions of copper sulfate (125 g $CuSO_4 \cdot 5H_2O$ in 500 g water) and sodium orthophosphate (134.3 g $Na_3PO_4 \cdot 12H_2O$ in 200 g water). Both solutions were first heated to 85° C. The phosphate was added rapidly to the stirred sulfate. The green solid was filtered, washed three times with water and dried in vacuo at 49° C. Analysis gave Cu=50.11 wt % and P=12.16 wt % corresponding to a Cu/P atom ratio of 2.01 in good agreement with that expected for $Cu_3(PO_4)_2 \cdot Cu(OH)_2$. Strong vibrations in the FTIR spectrum at 814 cm$^{-1}$, 959 cm$^{-1}$ and 1058 cm$^{-1}$ are in agreement with the published spectrua of the orthophosphate and basic phosphate (R. A. Nyquist and R. O. Nagel, Infrared Spectra of Inorganic Compounds, vol. 4, page 173, Academic Press, Boston, 1997). The x-ray powder diffraction pattern showed excellent agreement with a basic copper phosphate sample purchased from Aldrich (Cu/P=1.95).

TABLE 10

DATA FOR MULTIBATCH EXPERIMENT OF EXAMPLE 45A-45C

|  | EXAMPLE 45A | EXAMPLE 45B | EXAMPLE 45C |
|---|---|---|---|
| Si Conversion, % | 60.27 | 75.05 | 64.79 |
| Average Selectivity | 15.87 | 17.45 | 10.88 |
| Average Rate, % Si/h | 7.56 | 7.70 | 7.40 |
| MDMS, wt % | 1.85 | 1.55 | 1.11 |
| TMS, wt % | 88.76 | 88.99 | 86.40 |
| MTMS, wt % | 0.24 | 0.27 | 0.27 |
| TMOS, wt % | 5.59 | 5.10 | 7.94 |
| HVS, % | 3.56 | 4.09 | 4.28 |

Whereas TMOS increased >6 wt % during the third reaction of Example 45, it remained <6 wt % after five reactions of Example 46. The improved performance of Example 46 is attributable to the use of effective levels of basic copper phosphate in the experiments of that example. These effective levels also yield improved selectivity to TMS.

TABLE 11

CONTROL OF TMOS LESS THAN 6 WEIGHT PERCENT WITH COPPER PHOSPHATE IN MULTIBATCH DIRECT SYNTHESIS OF TMS

|  | Example 46A | Example 46B | Example 46C | Example 46D | Example 46E |
|---|---|---|---|---|---|
| Si Conv, % | 61.17 | 62.27 | 61.87 | 62.16 | 71.75 |
| Average Selectivity | 22.36 | 24.82 | 21.12 | 18.71 | 16.54 |
| Average Rate, % Si/h | 7.57 | 7.78 | 7.73 | 7.31 | 7.36 |
| MDMS, wt % | 2.27 | 2.26 | 1.97 | 1.70 | 1.77 |
| TMS, wt % | 90.10 | 90.16 | 90.48 | 90.01 | 89.24 |
| MTMS, wt % | 0.25 | 0.39 | 0.33 | 0.30 | 0.34 |
| TMOS, wt % | 4.03 | 3.63 | 4.29 | 4.81 | 5.40 |
| HVS, % | 3.35 | 3.55 | 2.94 | 3.17 | 3.25 |

(12) Examples 47A -47C and 48A -48E

These Examples illustrate the necessity of maintaining copper phosphate at effective levels during multibatch experiments (and by extension continuous operation) if TMOS is to be kept <6 wt % and TMS>87 wt %.

Example 47A -47C is the same as that of Example 26A -26C. Example 48A -48E was performed with the same SULCOSA Cu(OH)$_2$ (PO$_4^{3-}$=0.032 wt %) as was used in Example 47A-47C, but it was augmented with copper orthophosphate during the first two silicon charges. The copper orthophosphate (Rose Chemicals) had a Cu/P atom ratio of 1.6 (Cu=48.59 wt %, P=14.83 wt %). It was used at 4.02 wt % of the copper hydroxide during these reactions. No phosphate addition was made in the third, fourth and fifth silicon charges.

TABLE 12

DATA SUMMARY FOR EXAMPLES 47A-47C

|  | EXAMPLE 47A | EXAMPLE 47B | EXAMPLE 47C |
|---|---|---|---|
| Si Conversion, % | 73.16 | 73.28 | 61.95 |
| Average Selectivity | 16.14 | 13.21 | 11.83 |
| Average Rate, % Si/h | 8.13 | 8.14 | 7.99 |
| MDMS, wt % | 1.30 | 1.06 | 0.94 |
| TMS, wt % | 88.66 | 87.90 | 87.20 |
| MTMS, wt % | 0.24 | 0.26 | 0.26 |
| TMOS, wt % | 5.49 | 6.66 | 7.37 |
| HVS, % | 4.31 | 4.07 | 4.23 |

TABLE 13

DATA SUMMARY FOR EXAMPLES 48A-48E

|  | Example 48A | Example 48B | Example 48C | Example 48D | Example 48E |
|---|---|---|---|---|---|
| Si Conv, % | 76.44 | 75.00 | 58.76 | 59.18 | 60.72 |
| Average Selectivity | 20.39 | 18.55 | 15.51 | 12.28 | 9.58 |
| Average Rate, % Si/h | 7.64 | 7.37 | 7.12 | 6.12 | 6.75 |
| MDMS, wt % | 2.03 | 1.40 | 1.04 | 0.73 | 0.85 |
| TMS, wt % | 89.14 | 89.30 | 88.79 | 88.11 | 85.90 |
| MTMS, wt % | 0.37 | 0.25 | 0.24 | 0.17 | 0.30 |
| TMOS, wt % | 4.37 | 4.81 | 5.72 | 7.18 | 8.97 |
| HVS, % | 4.08 | 4.27 | 4.21 | 3.81 | 3.96 |

Consistent with the data already disclosed hereinabove, TMOS was reduced in Examples 48A and 48B compared with Example 47A -47C. However, an increase in TMOS occurred in Example 48C -48E following the suspension of copper phosphate addition. Thus, it is essential that effective levels of copper phosphate be maintained during multibatch syntheses so that TMOS remains desirably below 6 wt %.

(13) Examples 49A -49C

These examples illustrate improved performance of the SPIESS URANIA copper hydroxide used in Example 16 above brought about by the addition of copper orthophosphate. The copper hydroxide contained less than 100 ppm phosphate as received. Examples 49B and 49C also illustrate phosphate-induced increase in $CH_3SiH(OCH_3)_2$ formation.

Three trimethoxysilane Direct Synthesis experiments are summarized in these examples. Example 49A (same as Example 16) serves as the comparative control. Example 49B was done under the same set conditions, except that 0.6 g $Cu_3(PO_4)_2$ (Rose Chemicals) was added to the reactor along with 13.2 g $Cu(OH)_2$. Example 49B was taken to about 75% silicon conversion, recharged with additional silicon, copper hydroxide and copper phosphate and continued as Example 49C. The proportions of copper phosphate to copper hydroxide and copper hydroxide to silicon were maintained in the quantities of raw materials charged in Example 49C.

TABLE 14

IMPROVEMENT IN THE PERFORMANCE OF $Cu(OH)_2$ FROM SPIESS-URANIA CAUSED BY COPPER PHOSPHATE ADDITION.

|  | EXAMPLE 49A | EXAMPLE 49B | EXAMPLE 49C |
|---|---|---|---|
| Si Conversion, % | 75.35 | 75.64 | 78.13 |
| Average Selectivity | 13.96 | 23.04 | 23.31 |
| Average Rate, % Si/h | 6.70 | 8.40 | 7.62 |
| MDMS, wt % | 0.84 | 2.01 | 1.68 |
| TMS, wt % | 90.27 | 91.64 | 90.88 |
| MTMS, wt % | 0.00 | 0.23 | 0.23 |
| TMOS, wt % | 6.46 | 3.98 | 3.90 |
| HVS, % | 2.43 | 2.14 | 3.32 |

Table 14 shows that desirable selectivity to TMS was maintained with the use of copper phosphate in Examples 49B and 49C. TMOS was reduced by about forty percent in these experiments from the value in the control reaction (Example 49A). $CH_3SiH(OCH_3)_2$ was increased by at least a factor of two when copper phosphate was used compared to the control.

(14) Examples 50A-50C

These Examples illustrate the use of sodium phosphate dodecahydrate ($Na_3PO_4 \cdot 12H_2O$) to reduce TMOS formation to <6 wt % in the Direct Synthesis of trimethoxysilane.

Three separate batch experiments are presented. Example 50A is the comparative control in which a SULCOSA $Cu(OH)_2$ containing 0.05 wt % copper phosphate was used without sodium phosphate addition. 0.51 g $Na_3PO_4 \cdot 12H_2O$ (Aldrich) per 13.2 g $Cu(OH)_2$ was used in both Examples 50B and 50C. In Example 50C, the sodium phosphate and copper hydroxide were first heated together in 200 g Therminol® 59 and maintained at 250° C. for one hour. This mixture was subsequently added to the reactor with 1750 g silicon and additional Therminol® 59 solvent. Data are presented in Table 15.

Both Examples 50B and 50C show reductions in TMOS formation and increases in TMS and MDMS formation attendant to the use of sodium phosphate.

TABLE 15

REDUCED TMOS FORMATION WITH SODIUM PHOSPHATE

|  | EXAMPLE 50A | EXAMPLE 50B | EXAMPLE 50C |
|---|---|---|---|
| Si Conversion, % | 83.21 | 84.21 | 82.94 |
| Average Selectivity | 16.53 | 21.98 | 19.82 |
| Average Rate, % Si/h | 7.24 | 8.15 | 8.23 |
| MDMS, wt % | 1.52 | 1.87 | 1.93 |
| TMS, wt % | 89.40 | 91.13 | 90.63 |
| MTMS, wt % | 0.24 | 0.23 | 0.27 |
| TMOS, wt % | 5.40 | 4.15 | 4.57 |
| HVS, % | 3.50 | 2.61 | 2.60 |

(15) Examples 51A -51B

These examples illustrate the improvement in the selectivity of the Direct Synthesis of trimethoxysilane caused by the use of trimethyl phosphate in conjunction with a copper hydroxide that is low in phosphate content.

Two experiments are presented. Both were run under the standard conditions disclosed in Examples 1-21 above. A SULCOSA copper hydroxide (13.2 g) with 7 ppm phosphate was the source of catalytic copper in both cases. In the experiment of Example 51B, trimethyl phosphate (0.7 g) was injected (with pressurized nitrogen) into the reactor immediately prior to the start of the methanol flow. Table 16 presents the data summary for both experiments.

TABLE 16

REDUCTION OF TMOS FORMATION IN TMS DIRECT SYNTHESIS CAUSED BY TRIMETHYL PHOSPHATE

|  | EXAMPLE 51A | EXAMPLE 51B |
|---|---|---|
| Trimethyl Phosphate, g | 0 | 0.7 |
| Si Conversion, % | 57.76 | 83.27 |
| Average Selectivity | 13.55 | 23.56 |
| Average Rate, % Si/h | 7.64 | 7.19 |
| MDMS, wt % | 1.24 | 2.04 |
| TMS, wt % | 88.39 | 90.35 |
| MTMS, wt % | 0.21 | 0.32 |
| TMOS, wt % | 6.52 | 3.84 |
| HVS, % | 3.63 | 3.45 |

In Example 51A, TMOS formation spanned 5.5-7.6 wt % in the initial (<20 percent Si conversion) phase of the reaction. Thereafter, it remained between 4.5-5.5 wt %. TMOS content of the product mixture was greater than 6 wt %. In contrast, TMOS remained<5 wt % throughout the experiment of Example 51B. Clearly, the principal effects of trimethyl phosphate were a reduction in TMOS formation and increased selectivity to TMS. MDMS was also increased significantly.

(16) Examples 52A -52D

These examples illustrate the use of 400 ppm trimethyl phosphate to reduce TMOS formation, in the Direct Synthesis of trimethoxysilane, from greater than 6 wt % to desirable levels. The Examples also illustrate increases in MDMS induced by trimethyl phosphate.

In the experiment of Example 52B, 0.7 g trimethyl phosphate was added, along with additional copper hydroxide and silicon, to the residue of Example 31D to continue the multibatch experiment. Example 52A (same data as Example 31D) is shown for comparison. Similarly, Example 52D is the continuation of the multibatch experiment of Example 25 following addition of copper hydroxide, silicon and 0.7 g trimethyl phosphate to the residue of the experiment summarized above in Example 25C. Data for Example 31D are shown in Table 17 as Example 52A and those for Example 25C as Example 52C.

Example 52B shows that addition of trimethyl phosphate to the reaction slurry of Example 52A (Example 31 D) caused a reduction in TMOS from >6 wt % to <5 wt %. Likewise in Example 52D, trimethyl phosphate addition to Example 25C (Example 52C) effected a decrease in TMOS from >9 wt % to <6 wt %. These data illustrate the remedial effects of 400 ppm trimethyl phosphate (based on weight of silicon charged) on selectivity to trimethoxysilane. Simultaneously, methyldimethoxysilane was increased by at least forty percent over that in the control.

TABLE 17

DATA SUMMARY FOR EXAMPLES 52A-52D

| | Example 52A | Example 52B | Example 52C | Example 52D |
|---|---|---|---|---|
| Si Conv, % | 69.10 | 71.40 | 70.65 | 69.05 |
| Average Selectivity | 14.17 | 18.90 | 9.40 | 15.44 |
| Average Rate, % Si/h | 7.90 | 7.02 | 7.64 | 8.20 |
| MDMS, wt % | 1.19 | 1.71 | 0.64 | 1.68 |
| TMS, wt % | 88.69 | 88.92 | 85.79 | 88.46 |
| MTMS, wt % | 0.29 | 0.29 | 0.16 | 0.43 |
| TMOS, wt % | 6.26 | 4.76 | 9.12 | 5.73 |
| HVS, % | 3.57 | 3.32 | 4.28 | 3.69 |

(17) Examples 53A-53D

As is evident from Examples 52A -52D as well as Examples 22-31, TMOS generally increases during the course of multibatch experiments. Evidence gathered during this study shows that if the solvent is treated for removal of condensed silicates, desirable multibatch reaction performance can be restored provided that effective phosphate levels are maintained during subsequent reactions. Experimental results indicated that used, untreated solvent, such as is present in the latter reactions of a multibatch operation, detracts from desirable reaction performance. The presence of an organic or inorganic phosphate during the copper hydroxide thermal decomposition step, or later during the reaction with methanol, contributes to reliable reaction performance. The instant Examples illustrate the remedial effects of trimethyl phosphate (Example 53B), dimethyl phosphite (Example 53C) and tributyl phosphate (Example 53D) when the Direct Synthesis of trimethoxysilane is performed with copper hydroxide, which has been decomposed in used solvent that has not been treated for removal of condensed silicates.

Four experiments are summarized in these examples. All experiments were done with the PHIBROTECH copper hydroxide used previously in Examples 6 and 24. The quantities of raw materials used and the reaction conditions were the same as those disclosed above in Examples 1-19. Example 53A is a control experiment in which the copper hydroxide was decomposed in situ in fresh Therminole 59. In each of Examples 53B, 53C and 53D, 13.2 g of the same copper hydroxide was decomposed ex situ (see U.S. 2003/0051580 and U.S. 2003/0032829) at 250° C. in 250 g used, untreated Therminol® 59 from the commercial Direct Synthesis of trimethoxysilane (see Example 1, Table 3 in U.S. Pat. No. 6,090,965). The resulting mixture was combined with 3.25 kg fresh Therminol® 59 and used in the Direct Synthesis experiments.

The experiment of Example 53A was operated for 10 hours during which 78.23 percent of the silicon charged was converted to 6125.07 g crude product. This product had the composition: 1.38 wt % MDMS, 89.67 wt % TMS, 0.19 wt % MTMS, 4.72 wt % TMOS and 4.04 wt % HVS. Hydrogen evolution, indicative of the reaction of methanol with copper-activated silicon, was apparent from the outset. A steady-state existed between 11-71 percent silicon conversion. Temperature rose to 254-260° C. between 2.5-9.5 h.

The experiment of Example 53B was run for 10.5 hours. Hydrogen evolution was only intermittent during the first 4.5 hours. Temperature of the reactor remained at 249.4° C. -250° C. Analysis of samples indicated that only 1.2 percent silicon conversion occurred in that period. 92.40 g crude product containing 85.71 wt % TMS and 6.69 wt % TMOS was generated. Trimethyl phosphate (0.7 g) was then injected into the reactor and the reaction continued for another 6 hours. Hydrogen evolution increased and there was an exotherm, which raised the reactor temperature to 261.8° C. by the end of the experiment. Steady-state was established after 4 hours. 2447.09 g additional crude was formed in the 6 hours following trimethyl phosphate injection. Table 18 presents the analyses of samples taken at steady-state.

TABLE 18

REDUCED TMOS FORMATION AFTER (CH$_3$O)$_3$PO INJECTION

| | INITIAL 4.5 hr | 8.5 h | 9.5 h | 10.5 h |
|---|---|---|---|---|
| Si Conv, % | 1.2 | 15.48 | 24.07 | 32.61 |
| Selectivity | 12.81 | 19.30 | 25.74 | 24.61 |
| Average Rate, % Si/h | 0.27 | 1.82 | 2.53 | 3.11 |
| MDMS, wt % | 0 | 1.16 | 2.23 | 2.23 |
| TMS, wt % | 85.71 | 92.15 | 91.22 | 90.84 |
| MTMS, wt % | 0 | 0.20 | 0.29 | 0.29 |
| TMOS, wt % | 6.69 | 4.78 | 3.54 | 3.69 |
| HVS, % | 0 | 1.71 | 2.72 | 2.96 |

Comparison of the results of Examples 53A and 53B shows clearly that the Direct Synthesis reaction rate and selectivity were impaired when the copper hydroxide was decomposed in used, unremediated solvent. Addition of trimethyl phosphate increased both the reaction rate and selectivity of the trimethoxysilane Direct Synthesis. TMOS was reduced from greater than 6 wt % prior to trimethyl phosphate injection to 3-5 wt % in the steady-state period following the injection. TMS increased from less than 86 wt % to greater than 90 wt % and MDMS increased from zero to >2 wt % in the same period.

In the course of trimethoxysilane Direct Synthesis experiments during which trimethyl phosphate was added to the reaction, the distinct odor of an organophosphite was detected in some of the samples collected for gc analysis. GC/MS revealed the presence of dimethyl phosphite, (CH$_3$O)$_2$POH. Accordingly, its effect on the Direct Synthesis was also evaluated. The results are presented in Example 53C.

As was described above, copper hydroxide was decomposed separately in used, untreated Therminol® 59 for use in the experiment of this Example. Dimethyl phosphite (0.96 g) was added to the Direct Synthesis reaction after 1.75 hours. Up to that point, the reaction had been very slow with selectivity <5. Whereas 128.95 g Si (7.37 percent conversion) had been converted to crude product in 1.5 hours of the control experiment (Example 52A), only 19.84 g Si (1.13 percent conversion) had reacted in the same time of Example 52C. Both reaction rate and selectivity increased markedly following addition of dimethyl phosphite. The reaction temperature increased from 250° C. to 254.3° C. in the hour following addition of dimethyl phosphate. Temperature remained 260° C.-263° C. from the 3.75 hour mark to the end of the experiment at 9.75 hours (69.28 percent silicon conversion). The data are summarized in Table 19.

Table 19 shows the marked improvement in the principal reaction indices following introduction of about 550 ppm dimethyl phosphite (based on weight of silicon charged). Notably, TMS increased from less than 80 wt % to greater than 88 wt %. TMOS decreased from greater than 17 wt % to less than 5 wt % and selectivity was in the range, 18-23. Additionally, MDMS was increased from zero to 1-3.5 wt %. Thus, like trimethyl phosphate, dimethyl phosphite can negate and reverse the effects of the buildup of condensed silicates in the Direct Synthesis reaction slurry.

It is clear from these data that tributyl phosphate decreases TMOS and increases TMS and MDMS and reaction rate to acceptable levels.

(18) Examples 54A -54C

These examples illustrate the use of effective levels of both copper phosphate and trimethyl phosphate in maintaining TMOS below 6 wt % and sustaining reaction stability and selectivity to TMS during multibatch operation.

A SULCOSA copper hydroxide containing 9.8 ppm phosphate, employed hereinabove in Example 9, was used in the three batches of this experiment. The first batch (Example 54A) was run with 12.39 g copper hydroxide, 1 g $Cu_3(PO_4)_2 \cdot 2H_2O$ (Fluka) and 1750 g silicon. Succeeding batches were continued with trimethyl phosphate. 0.35 g trimethyl phosphate, 9.912 g copper hydroxide and 1400 g silicon were added to the residue of Example 54A to continue Example 54B. Similarly, 0.18 g trimethyl phosphate, 9.295 g copper hydroxide and 1312.5 g silicon were added to the residue of Example 54B for the start of the third batch (Example 54C). In Examples 54B and 54C, trimethyl phosphate was injected with nitrogen pressure just prior to the start of methanol flow. The copper phosphate used contained 45.84 wt % Cu and 14.51 wt % P. The Cu/P atom ratio was 1.54 in good agreement with the expected value of 1.5. The x-ray powder diffraction pattern matched that published for the authentic orthophosphate. Table 21 presents the experimental Direct Synthesis data.

TABLE 19

REDUCED TMOS FORMATION AFTER $(CH_3O)_2POH$ INJECTION

|  | 0-1.5 h | 3.25 h | 3.75 h | 4.25 h | 5.25 h | 6.25 h | 7.25 h | 8.25 h |
|---|---|---|---|---|---|---|---|---|
| Temp, ° C. | 250.2 | 258.1 | 260.2 | 261.1 | 261.7 | 261.4 | 262.7 | 260.5 |
| Si Conv, % | 1.13 | 13.06 | 17.39 | 21.82 | 30.74 | 39.70 | 48.53 | 57.05 |
| Selectivity | 4.62 | 18.09 | 19.51 | 22.19 | 22.97 | 22.37 | 20.73 | 18.62 |
| Average Rate, % Si/h | 0.76 | 4.02 | 4.64 | 5.13 | 5.86 | 6.35 | 6.69 | 6.92 |
| MDMS, wt % | 0 | 3.35 | 3.45 | 2.99 | 2.44 | 1.99 | 1.69 | 1.38 |
| TMS, wt % | 79.64 | 87.57 | 87.38 | 88.76 | 89.31 | 89.69 | 89.87 | 89.20 |
| MTMS, wt % | 0 | 0.55 | 0.55 | 0.45 | 0.38 | 0.34 | 0.32 | 0.30 |
| TMOS, wt % | 17.23 | 4.84 | 4.48 | 4.00 | 3.89 | 4.01 | 4.33 | 4.79 |
| HVS, % | 3.13 | 3.68 | 4.13 | 3.81 | 3.97 | 3.97 | 3.79 | 4.32 |

The experiment of Example 53D was performed in a similar manner to those of Examples 53B and 53C, except that tributyl phosphate (1.33 g) was injected at the 1.75 hour mark of the reaction. Only 36.66 g Si (2.09 percent conversion) had reacted in the first 1.5 hours. The reaction mixture contained greater than 16 wt % TMOS. A sample taken 15 minutes after the injection of tributyl phosphate contained 21.68 wt % TMOS, but another taken 15 minutes later showed a decrease to 9.40 wt % TMOS. Table 20 shows that thereafter, the product composition was acceptably stable.

TABLE 20

REDUCED TMOS FORMATION AFTER $(C_4H_9O)_3PO$ INJECTION

|  | 0-1.5 h | 2.75 h | 3.25 h | 4.00 h | 5.00 h | 6.50 h | 7.50 h | 8.75 h |
|---|---|---|---|---|---|---|---|---|
| Temp, ° C. | 250.5 | 253.9 | 258.2 | 260.5 | 261.8 | 262.7 | 262.3 | 261.6 |
| Si Conv, % | 2.09 | 11.11 | 15.46 | 22.06 | 30.92 | 44.33 | 53.15 | 63.87 |
| Selectivity | 4.99 | 18.64 | 18.57 | 20.65 | 23.68 | 25.97 | 25.91 | 26.17 |
| Average Rate, % Si/h | 1.40 | 4.04 | 4.76 | 5.52 | 6.18 | 6.82 | 7.09 | 7.30 |
| MDMS, wt % | 0.41 | 1.48 | 3.19 | 3.57 | 3.44 | 3.17 | 3.14 | 2.71 |
| TMS, wt % | 80.68 | 91.43 | 88.42 | 88.10 | 89.19 | 89.88 | 89.65 | 89.91 |
| MTMS, wt % | 0.46 | 0.35 | 0.68 | 0.61 | 0.51 | 0.40 | 0.38 | 0.33 |
| TMOS, wt % | 16.17 | 4.90 | 4.76 | 4.27 | 3.77 | 3.46 | 3.46 | 3.44 |
| HVS, % | 2.28 | 1.84 | 2.96 | 3.45 | 3.09 | 3.09 | 3.37 | 3.62 |

TABLE 21

MULTIBATCH EXPERIMENT WITH $Cu_3(PO_4)_2$ AND $(CH_3O)_3PO$

|  | EXAMPLE 54A | EXAMPLE 54B | EXAMPLE 54C |
|---|---|---|---|
| Additive, g | 1 g $Cu_3(PO_4)_2 \cdot 2H_2O$ | 0.35 g $(CH_3O)_3P=O$ | 0.18 g $(CH_3O)_3P=O$ |
| Si Conv, % | 74.13 | 69.72 | 84.16 |
| Selectivity | 26.33 | 22.74 | 18.72 |
| Average Rate, % Si/h | 8.16 | 8.37 | 7.39 |
| MDMS, wt % | 2.06 | 1.98 | 1.11 |
| TMS, wt % | 91.17 | 90.20 | 90.40 |
| MTMS, wt % | 0.31 | 0.32 | 0.19 |
| TMOS, wt % | 3.46 | 3.97 | 4.83 |
| HVS, % | 3.00 | 3.53 | 4.67 |

The product mixture from the single batch reaction (Example 9) with the SULCOSA copper hydroxide contained 4.95 wt % TMOS. Addition of approximately 8 wt % copper phosphate to the copper hydroxide afforded a reduction to 3.46 wt % TMOS in the reaction mixture of Example 54A. The presence of 100-200 ppm trimethyl phosphate in Examples 54C and 54B, respectively, was sufficient to maintain TMOS<5 wt % in the course of the next two batch reactions. The data also confirm the dependence of MDMS on adequate phosphate concentration.

(19) Examples 55A -55C

These examples show that the use of copper phosphate as the sole source of catalytic copper in the Direct Synthesis of trimethoxysilane affords TMOS greater than 6 wt %.

Three experiments are summarized in these examples. Example 55A was run with 18.52 g $Cu_3(PO_4)_2 \cdot 2H_2O$ (Fluka) and 1750 g silicon. Examples 55B and 55C used basic copper phosphate (Aldrich $Cu_3(PO_4)_2 \cdot Cu(OH)_2$) with the same weight of silicon. 13.2 g basic copper phosphate was used in Example 55B and 66 g in Example 55C. Example 55C was the continuation of Example 55B following the addition of silicon and basic copper phosphate to the reaction residue. All other set conditions were as set forth in Examples 1-21 and Examples 22-32. The data are presented in Table 22.

TABLE 22

DIRECT SYNTHESIS OF TMS WITH COPPER PHOSPHATE AS ONLY SOURCE OF CATALYTIC COPPER

|  | EXAMPLE 55A | EXAMPLE 55B | EXAMPLE 55C |
|---|---|---|---|
| Copper Source, g | $Cu_3(PO_4)_2 \cdot 2H_2O$, 18.52 g | $Cu_3(PO_4)_2 \cdot Cu((OH)_2$, 13.2 g | $Cu_3(PO_4)_2 \cdot Cu(OH)_2$, 66 g |
| Si Conv, % | 12.85 | 27.83 | 10.11 |
| Reaction Time, h | 5.75 | 7.5 | 3.5 |
| Product Yield, g | 1104.68 | 2354.92 | 881.52 |
| MDMS, wt % | 0.64 | 0.61 | 1.70 |
| TMS, wt % | 52.49 | 54.75 | 39.13 |
| MTMS, wt % | 1.17 | 0.99 | 4.05 |
| TMOS, wt % | 37.70 | 39.03 | 49.92 |
| HVS, % | 7.99 | 4.62 | 5.19 |
| Selectivity | 1.39 | 1.40 | 0.78 |

In the experiment of Example 55A, the weight of $Cu_3(PO_4)_2 \cdot 2H_2O$ was chosen so that the copper concentration of the slurry (relative to silicon) would be approximately 0.5 wt %, which is known to be an effective value when copper hydroxide is the source of catalytic copper. The experimental data confirm that the Direct Synthesis of trimethoxysilane did occur with copper phosphate as the source of copper for activation of silicon. However, the reaction was slow (2.23% Si conv/h) and the product contained 37.70 wt % TMOS. GC/MS disclosed $H_2Si(OCH_3)_2$ in addition to the main products shown in Table 18. The slow rate and high TMOS suggest that there were insufficient active sites for TMS formation. Accordingly, the excess methanol converted a considerable portion of the TMOS formed to TMOS via the consecutive reaction shown in equation [2] above.

Although rates were slightly higher when basic copper phosphate was used in Examples 55B and 55C, the conclusions just recited remain unchanged. Thus, the copper phosphates are effective promoters of selectivity to TMS and afford product with less than 6 wt % TMOS when used in combination with copper hydroxide, but they are ineffective as selective catalysts when used alone.

Samples collected during the experiments of these examples showed vigorous gas evolution, even when cooled in dry-ice. A pungent organophosphite odor also emanated from them. GC/MS analysis of selected samples established the presence of both trimethyl phosphate and dimethyl phosphite. The equations below are possible pathways by which these compounds might have been formed. If copper (II) methoxide is formed as an intermediate, it will decompose to nanosized copper as has been disclosed previously (see U.S. 2003/0051580 and U.S. 2003/0032829):

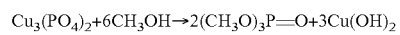

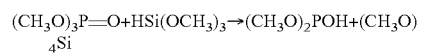

The following prior disclosures have been incorporated by reference herein are annexed hereto and are to be considered an integral part of the specification: U.S. Pat. Nos. 1,867,357; 1,800,828; 2,525,242; 2,924,505; 3,194,749; 3,428,731; 4,490,337; 4,727,173; 4,761,492; 4,808,406; 4,999,446; 5,084,590; 5,166,384; 6,166,237; 6,090,965; Re. 24,324; and, Published U.S. Patent Application 2002/0136685.

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

The invention claimed is:

1. A process for the Direct Synthesis of trialkoxysilane which comprises conducting the Direct Synthesis reaction of silicon and alcohol, optionally in solvent, in the presence of a mixture of a catalytically effective amount of Direct Synthesis catalyst precursor and an effective catalyst-promoting amount of Direct Synthesis catalyst promoter, said promoter being a mixture of organic and inorganic compound possessing at least one phosphorus-oxygen bond wherein a Direct Synthesis catalyst is produced in-situ by the reaction of the Direct Synthesis catalyst precursor with silicon.

2. The process of claim 1 wherein the trialkoxysilane possesses the general formula $HSi(OR)_3$ wherein each R is the same or different alkyl of from 1 to 6 carbon atoms.

3. The process of claim 2 wherein R is methyl, ethyl, propyl or isopropyl.

4. The process of claim 2 resulting in at least one additional reaction product selected from the group consisting of $Si(OR)_4$, $RSi(OR)_3$, $(RO)_3SiOSi(OR)_3$, $H(RO)_2SiOSi(OR)_2H$, $HSi(RO)_2SiOSi(OR)_3$, $(RO)_3SiOSi(OR)_2R$, $(RO)_3SiOSi(RO)_2OSi(RO)_3$, $(RO)_3SiOSi(OR)HOSi(OR)_3$, $(RO)_3SiOSi(OR)ROSi(OR)_3$, $(RO)Si[OSi(OR)_3]_3$, $(RO)_3SiOSi(OR)(OSi(RO)_3)OSi(OR)_3$ and $[OSi(OR)_2]_n$, wherein n is at least 4.

5. The process of claim 1 wherein the Direct Synthesis catalyst is obtained by contacting silicon and at least one member of the group consisting of copper and copper-containing compound.

6. The process of claim 1 wherein the Direct Synthesis catalyst is at least one member selected from the group consisting of copper-silicon alloy, intermetallic of copper and silicon, silicon containing diffused copper, reaction product of silicon and copper-containing compound.

7. The process of claim 5 wherein the copper-containing compound is at least one member of the group consisting of copper (I) oxide, copper (II) oxide, copper (I) chloride, copper (II) chloride, copper (II) hydroxide, mixed hydrous oxides, basic copper carbonate, copper carboxylate, copper alkoxide and copper siloxide.

8. The process of claim 6 wherein the copper-containing compound is at least one member of the group consisting of copper (I) oxide, copper (II) oxide, copper (I) chloride, copper (II) chloride, copper (II) hydroxide, mixed hydrous oxides, basic copper carbonate, copper carboxylate, copper alkoxide and copper siloxide.

9. The process of claim 1 wherein the Direct Synthesis catalyst possesses a particle size within the range of from about 0.1 to about 100 nanometers.

10. The process of claim 5 wherein the Direct Synthesis catalyst possesses a particle size within the range of from about 0.1 to about 100 nanometers.

11. The process of claim 6 wherein the Direct Synthesis catalyst possesses a particle size within the range of from about 0.1 to about 100 nanometers.

12. The process of claim 1 wherein the Direct Synthesis catalyst is substantially anhydrous.

13. The process of claim 5 wherein the Direct Synthesis catalyst is substantially anhydrous.

14. The process of claim 6 wherein the Direct Synthesis catalyst is substantially anhydrous.

15. The process of claim 1 wherein the Direct Synthesis catalyst promoter possessing at least one phosphorus-oxygen bond is at least one phosphorus-containing compound selected from the group consisting of phosphate salt, phosphate ester, polyphosphate, metaphosphate, pyrophosphate, phosphonate and phosphite.

16. The process of claim 15 wherein the phosphorus-containing compound contains at least one $PO_4^{3-}$, $P_2O_7^{2-}$, $P_3O_{10}^{5-}$, $P_{n+1}O_{3n+4}^{(n+3)-}$ wherein n is at least 4 and $P_xO_{3x}^{x-}$ wherein x is at least 3.

17. The process of claim 15 wherein the phosphorus-containing compound is at least one copper-containing compound selected from the group consisting of copper orthophosphate, copper metaphosphate and copper polyphosphate.

18. The process of claim 1 wherein the Direct Synthesis catalyst promoter possesses a particle size within the range of from about 0.1 to about 600 nanometers.

19. The process of claim 15 wherein the Direct Synthesis catalyst promoter possesses a particle size within the range of from about 0.1 to about 600 nanometers.

20. The process of claim 9 wherein the Direct Synthesis catalyst promoter possesses a particle size within the range of from about 0.1 to about 600 nanometers.

21. The process of claim 1 wherein the Direct Synthesis catalyst promoter is substantially anhydrous.

22. The process of claim 12 wherein the Direct Synthesis catalyst promoter is substantially anhydrous.

23. The process of claim 4 wherein the Direct Synthesis catalyst promoter is present in the reaction medium in an amount effective to limit $Si(OR)_4$ formation to below about 6 weight percent and to provide $HSi(OR)_3$ formation of greater than about 85 weight percent based on the total weight of silane products.

24. The process of claim 1, wherein the effective catalyst-promoting amount of Direct Synthesis catalyst promoter is from 3 to 30 weight percent, based on the weight of copper catalyst precursor.

25. A process for the Direct Synthesis of trialkoxysilane which comprises conducting the Direct Synthesis reaction of silicon and alcohol, optionally in solvent, in the presence of a mixture of a catalytically effective amount of Direct Synthesis catalyst precursor selected from the group consisting of copper (I) oxide, copper (II) oxide, copper (I) carbonate, copper carboxylate, copper alkoxide and copper siloxide and an effective catalyst-promoting amount of Direct Syntheses catalyst promoter, said promoter being a mixture of organic and inorganic compounds possessing at least on phosphorus-oxygen bond is at least one phosphorus-containing compound selected from the group consisting of phosphate salt, phosphate ester, polyphosphate, metaphosphate, pyrophosphate, phosphonate and phosphite, wherein the Direct Synthesis catalyst promoter is from 3 to 30 weight percent based upon the weight of copper catalyst precursor, wherein a Direct Synthesis catalyst is produced in-situ by the reaction of the Direct Synthesis catalyst precursor with silicon.

26. The process of claim 25 wherein the phosphorus-containing Compound contains at least one $PO_4^{3-}$, $P_2O_7^{2-}$, $P_3O_{10}^{5-}$, $P_{n+1}O_{3n+4}^{(n+3)-}$ ion wherein n is at least 4 and $P_xO_{3x}^{x-}$ wherein x is at least 3.

27. The process according to claim 25 wherein the Direct Synthesis catalyst promoter is of the general formula:

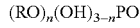

$(RO)_n(OH)_{3-n}PO$ wherein R is $C_1$ to $C_{20}$ alkyl, cylcoaliphatic or alkaryl and n is an integer from 0 to 3.

28. The process according to claim 25 wherein the Direct Synthesis catalyst promoter is of the general formula:

$MD_xD^*_yM$ wherein M is $(CH_3)_3SiO_{1/2}$; D is $(CH_3)_2SiO_{2/2}$; D* is $(CH_3)SiZO_{2/2}$; Z is a phosphorlyated oxyalkylene group; and x and y are greater than zero.

29. The process according to claim 25 wherein the Direct Synthesis catalyst promoter is of the general formula:

$M^*D_uD^*_yM^*$ wherein M* is $Z(CH_3)_2SiO_{1/2}$; D is $(CH_3)_2SiO_{2/2}$; D* is $(CH_3)SiZO_{2/2}$; Z is phosphorlyated oxyalkylene group; u is greater than zero; and v is greater than or equal to zero.

30. The process according to claim 25 wherein the Direct Synthesis catalyst promoter is of the general formula:

$$(ROSi)_w(R'OP{=}O)_z$$

wherein R is $C_1$ to $C_{20}$ alkyl, cylcoaliphatic or alkaryl; R' is $C_1$ to $C_{20}$ alkyl, cylcoaliphatic or alkaryl; and each w and z is an integer from 0.5 to 25.

31. The process according to claim 25 wherein the Direct Synthesis catalyst promoter is of the general formula:

$$(RO)_mP_2O_3(OH)_{4-m}$$

wherein R is $C_1$ to $C_{20}$ alkyl, cylcoaliphatic or alkaryl; and m is greater than or equal to 2.

32. The process according to claim 25 wherein the trialkoxysilane possesses the general formula $HSi(OR)_3$ wherein each R is the same or different alkyl of from 1 to 6 carbon atoms.

33. The process of claim 32 wherein R is methyl.

34. The process of claim 25 wherein the catalytically effective amount of Direct Synthesis catalyst precursor is from about 0.01 to about 5 parts by weight of catalyst precursor per 100 parts by weight of silicon metal.

* * * * *